(12) United States Patent
Soreefan et al.

(10) Patent No.: US 12,176,105 B2
(45) Date of Patent: Dec. 24, 2024

(54) PATIENT MONITORING SYSTEM

(71) Applicant: Hill-Rom Services, Inc., Batesville, IN (US)

(72) Inventors: Ibne Soreefan, West Chester, OH (US); Tyler Holmes, Monroe, CT (US); Eric Dustin Agdeppa, Cary, NC (US)

(73) Assignee: Hill-Rom Services, Inc., Batesville, IN (US)

(*) Notice: Subject to any disclaimer, the term of this patent is extended or adjusted under 35 U.S.C. 154(b) by 63 days.

(21) Appl. No.: 17/891,188

(22) Filed: Aug. 19, 2022

(65) Prior Publication Data

US 2023/0057855 A1 Feb. 23, 2023

Related U.S. Application Data

(60) Provisional application No. 63/235,912, filed on Aug. 23, 2021.

(51) Int. Cl.
*G16H 40/67* (2018.01)
*G06V 10/25* (2022.01)
(Continued)

(52) U.S. Cl.
CPC ............. *G16H 40/67* (2018.01); *G06V 10/25* (2022.01); *G06V 20/52* (2022.01); *G06V 40/161* (2022.01); *G06V 2201/07* (2022.01)

(58) Field of Classification Search
CPC ........ G16H 40/67; G16H 80/00; G16H 30/20; G16H 40/63; G16H 20/40; G16H 30/40;
(Continued)

(56) References Cited

U.S. PATENT DOCUMENTS 6,061,088 A 5/2000 Khosravi et al.
6,570,608 B1 5/2003 Tserng
(Continued)

FOREIGN PATENT DOCUMENTS

CN 104434033 A 3/2015
CN 109948433 A 6/2019
(Continued)

OTHER PUBLICATIONS

Hu, et al., "Combination of Near-Infrared and Thermal Imaging Techniques for the Remote and Simultaneous Measurements of Breathing and Heart Rates Under Sleep Situation" Plos One, Jan. 5, 2018, pp. 1-14.
(Continued)

*Primary Examiner* — Michael Lee
(74) *Attorney, Agent, or Firm* — Price Heneveld LLP

(57) ABSTRACT

A contactless patient monitoring system includes a first imager configured to capture first image data of a target area within a first field of view. A second imager is operably coupled to the first imager. The second imager is configured to capture second image data of the target area within a second field of view. An emitter is operably coupled to at least one of the first imager and the second imager. The emitter is configured to emit light within a predetermined wavelength range. A controller is communicatively coupled to the first imager, the second imager, and the emitter. The controller is configured to determine a facial region of a person in the first image data, determine a region of interest in the second image data that coincides with the facial region in the first image data, and determine a coordinate of a head position within the facial region.

19 Claims, 24 Drawing Sheets

(51) Int. Cl.
*G06V 20/52* (2022.01)
*G06V 40/16* (2022.01)

(58) Field of Classification Search
CPC ...... G06V 10/25; G06V 20/52; G06V 40/161; G06V 2201/07; G06V 40/15; A61B 5/015; A61B 5/024; A61B 5/0816; A61B 5/0037; A61B 5/0077; A61B 5/1176
See application file for complete search history.

(56) References Cited

U.S. PATENT DOCUMENTS

| | | | |
|---|---|---|---|
| 6,633,232 B2 | 10/2003 | Trajkovic et al. | |
| 7,987,069 B2 | 7/2011 | Rodgers et al. | |
| 8,149,273 B2 | 4/2012 | Liu et al. | |
| 8,542,872 B2 | 9/2013 | Gornick et al. | |
| 8,571,261 B2 | 10/2013 | Gagvani et al. | |
| 9,301,689 B2 | 4/2016 | Vanderpohl | |
| 9,560,974 B2 | 2/2017 | Tolosa et al. | |
| 9,750,420 B1 | 9/2017 | Agrawal et al. | |
| 9,928,607 B2 * | 3/2018 | Jeanne | A61B 5/7207 |
| 9,962,095 B2 | 5/2018 | Ahmad et al. | |
| 10,159,443 B2 | 12/2018 | Bresch et al. | |
| 10,258,242 B2 | 4/2019 | Godavaarty et al. | |
| 10,806,356 B2 | 10/2020 | Lee et al. | |
| 10,904,492 B2 | 1/2021 | Derenne et al. | |
| 11,882,366 B2 * | 1/2024 | Soreefan | A61B 5/7485 |
| 2004/0100563 A1 | 5/2004 | Sablak et al. | |
| 2005/0286741 A1 | 12/2005 | Watanabe et al. | |
| 2009/0066790 A1 | 3/2009 | Hammadou | |
| 2009/0161981 A1 | 6/2009 | Allen | |
| 2009/0310862 A1 | 12/2009 | Tu et al. | |
| 2010/0316257 A1 | 8/2010 | Xu et al. | |
| 2010/0290710 A1 | 11/2010 | Gagvani et al. | |
| 2011/0102627 A1 | 1/2011 | Okada et al. | |
| 2011/0134245 A1 | 6/2011 | Khizhnichenko | |
| 2012/0078088 A1 | 3/2012 | Whitestone et al. | |
| 2012/0081552 A1 | 4/2012 | Sablak et al. | |
| 2012/0283530 A1 | 11/2012 | Maynard et al. | |
| 2014/0085545 A1 | 3/2014 | Tu et al. | |
| 2014/0253709 A1 * | 9/2014 | Bresch | H04N 7/18 348/77 |
| 2014/0254670 A1 | 9/2014 | Kwon et al. | |
| 2014/0275832 A1 | 9/2014 | Muehlsteff et al. | |
| 2015/0023552 A1 | 1/2015 | Rosen | |
| 2015/0178953 A1 | 6/2015 | Gao et al. | |
| 2015/0294549 A1 | 10/2015 | Ribble | |
| 2015/0312575 A1 | 10/2015 | Bryant | |
| 2016/0166333 A1 * | 6/2016 | Wang | A61B 34/10 600/476 |
| 2017/0220870 A1 | 8/2017 | Roth et al. | |
| 2018/0132797 A1 * | 5/2018 | Draeger | A61B 5/1075 |
| 2019/0000391 A1 | 1/2019 | De Haan et al. | |
| 2019/0075302 A1 | 3/2019 | Huang et al. | |
| 2019/0108387 A1 * | 4/2019 | Rivard | G06T 7/40 |
| 2020/0105407 A1 * | 4/2020 | Soreefan | G08B 21/0461 |
| 2020/0155040 A1 * | 5/2020 | Soreefan | A61B 5/746 |
| 2020/0178809 A1 | 6/2020 | Wang et al. | |
| 2020/0219604 A1 * | 7/2020 | Hallack | G06V 10/143 |
| 2020/0234439 A1 | 7/2020 | Chang et al. | |
| 2020/0297247 A1 | 9/2020 | Clark et al. | |
| 2020/0367762 A1 | 11/2020 | Wallace | |
| 2021/0369122 A1 * | 12/2021 | Lane | A61B 5/743 |
| 2022/0101847 A1 * | 3/2022 | Receveur | H04R 5/02 |
| 2022/0202315 A1 * | 6/2022 | Soreefan | A61B 5/0002 |
| 2022/0313112 A1 * | 10/2022 | Wolfe | A61B 5/02055 |

FOREIGN PATENT DOCUMENTS

| | | |
|---|---|---|
| CN | 110060272 A | 7/2019 |
| EP | 2994880 B1 | 6/2017 |
| EP | 3207862 A1 | 8/2017 |
| KR | 101426750 B1 | 8/2014 |
| WO | 2017146643 A1 | 8/2017 |
| WO | 2020137276 A1 | 2/2020 |
| WO | 2020052626 A1 | 3/2020 |

OTHER PUBLICATIONS

Nam, et al., "Monitoring of Heart and Breathing Rates Using Dual Cameras on a Smartphone", PLoS ONE 11(3), Mar. 10, 2016, pp. 1-15.

* cited by examiner

PATIENT MONITORING SYSTEM

CROSS-REFERENCE TO RELATED APPLICATION

This application claims priority to and the benefit under 35 U.S.C. § 119 (e) of U.S. Provisional Application No. 63/235,912, filed on Aug. 23, 2021, entitled "PATIENT MONITORING SYSTEM," the disclosure of which is hereby incorporated herein by reference in its entirety.

FIELD OF THE DISCLOSURE

The present disclosure generally relates to a monitoring system, and more particularly to a contactless patient monitoring system for a medical facility.

SUMMARY OF THE DISCLOSURE

According to one aspect of the present disclosure, a contactless patient monitoring system includes a first imager configured to capture first image data of a target area within a first field of view. A second imager is operably coupled to the first imager. The second imager is configured to capture second image data of the target area within a second field of view. An emitter is operably coupled to at least one of the first imager and the second imager. The emitter is configured to emit light within a predetermined wavelength range. A controller is communicatively coupled to the first imager, the second imager, and the emitter. The controller is configured to determine a facial region of a person in the first image data, determine a region of interest in the second image data that coincides with the facial region in the first image data, and determine at least one coordinate of a head position within the facial region.

According to another aspect of the present disclosure, a patient monitoring system includes a housing. A thermal imager is configured to obtain thermal image data within first a field of view. A monochromatic imager is configured to obtain monochromatic image data within a second field of view. At least one side imager assembly is selectively coupled to the housing via an actuator. The at least one side imager assembly is configured to obtain image data within a side field of view. A controller is communicatively coupled to the thermal imager, the monochromatic imager, and the at least one imager and the at least one side imager assembly. The controller is configured to activate the at least one side imager assembly in response to movement of a person within at least one of the first field of view and the second field of view toward the side field of view.

According to another aspect of the present disclosure, a monitoring system includes a housing. A first side imager assembly is selectively coupled to a first side of the housing. The first side imager assembly defines a first side field of view to capture image data. A second side imager assembly is selectively coupled to a second side of the housing. The second side imager assembly defines a second side field of view to capture image data. At least one imager is coupled to the housing and defines a field of view to capture image data. The field of view overlaps with at least one of the first side field of view and the second side field of view. A controller is communicatively coupled with the at least one imager, the first side imager assembly, and the second side imager assembly to receive the image data. The controller is configured to monitor movement within the field of view, the first side field of view, and the second side field of view and adjust an orientation of at least one of the first side imager assembly and the second side imager assembly in response to the movement.

These and other features, advantages, and objects of the present disclosure will be further understood and appreciated by those skilled in the art by reference to the following specification, claims, and appended drawings.

DETAILED DESCRIPTION

Figure 1:
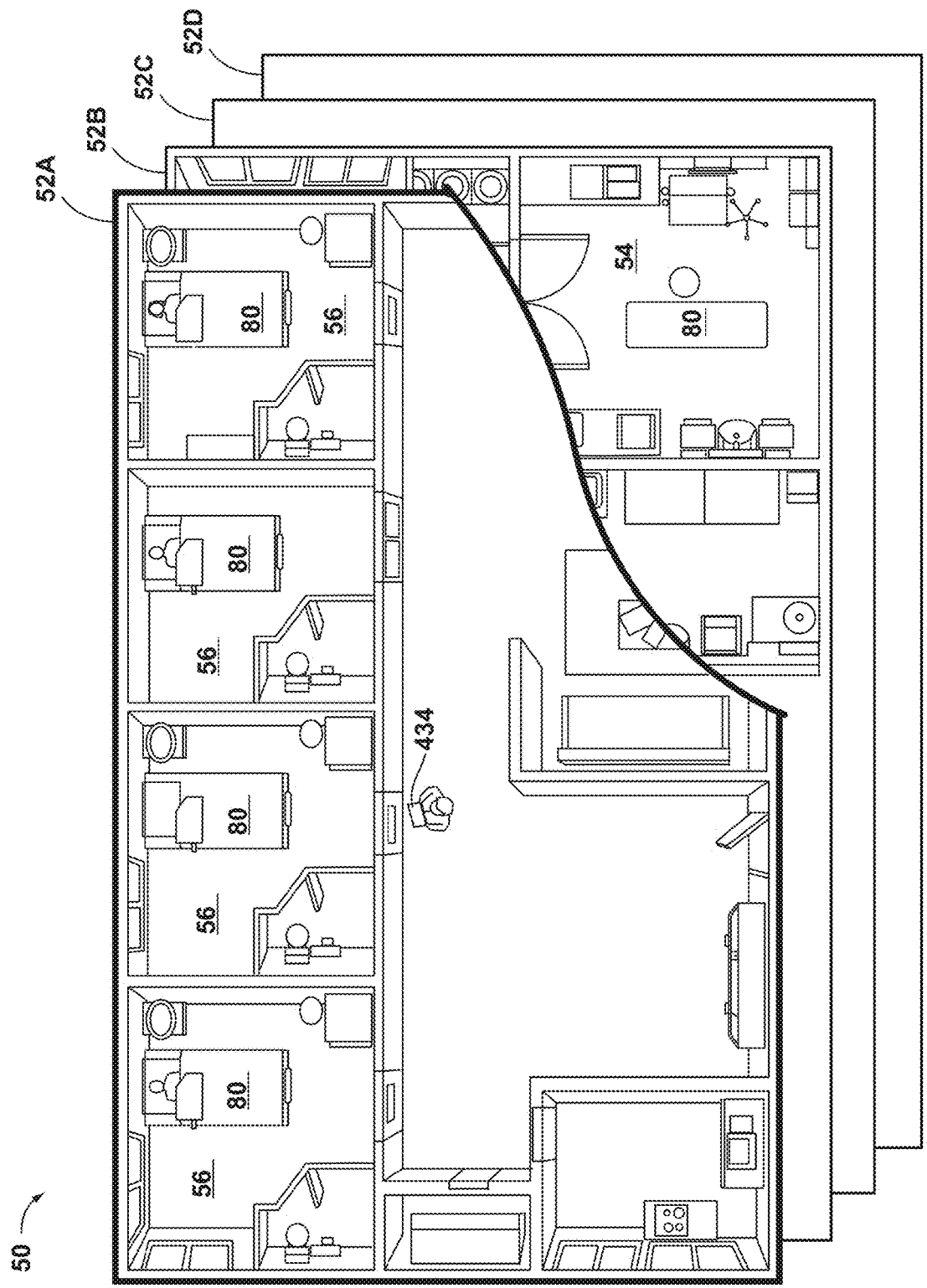
FIG. 1 is a schematic diagram of a portion of a medical facility, according to the present disclosure.

The present illustrated embodiments reside primarily in combinations of method steps and apparatus components related to a patient monitoring system. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-31, reference numeral 10 generally designates a contactless patient monitoring system that includes a first imager 12 configured to capture first image data 14 of a target area 16 within a first field of view 18. A second imager 20 is operably coupled to the first imager 12 and is configured to capture second image data 22 of the target area 16 within a second field of view 24. An emitter 26 is operably coupled to at least one of the first imager 12 and the second imager 20. The emitter 26 is configured to emit light 28 within a predetermined wavelength range. A controller 30 is communicatively coupled to the first imager 12, the second imager 20, and the emitter 26. The controller 30 is configured to determine a facial region 32 of a person in the first image data 14. The controller 30 is also configured to determine a region of interest (ROI) 34 in the second image data 22 that coincides with the facial region 32 in the first image data 14. Additionally, the controller 30 is configured to determine at least one coordinate of a head position 36 within the facial region 32.

Referring to FIG. 1, a person may become a patient at a medical facility 50 for treatment, for a procedure, for monitoring, or for receiving other types of care. The patient may be transported between several areas or units while at the medical facility 50. While at the medical facility 50, the patient may be transferred between different departments on different floors 52A-52D within the medical facility 50 depending on the treatment or procedure to be received. For example, the patient may be transported between a surgical suite 54 for one or more surgical procedures and a patient room 56 for recovery and monitoring. Depending on the care to be received by the patient, the patient may stay at the medical facility 50 for a period of time. In such circumstances, the patient may stay in the patient room 56 for monitoring and care.

Figure 2:
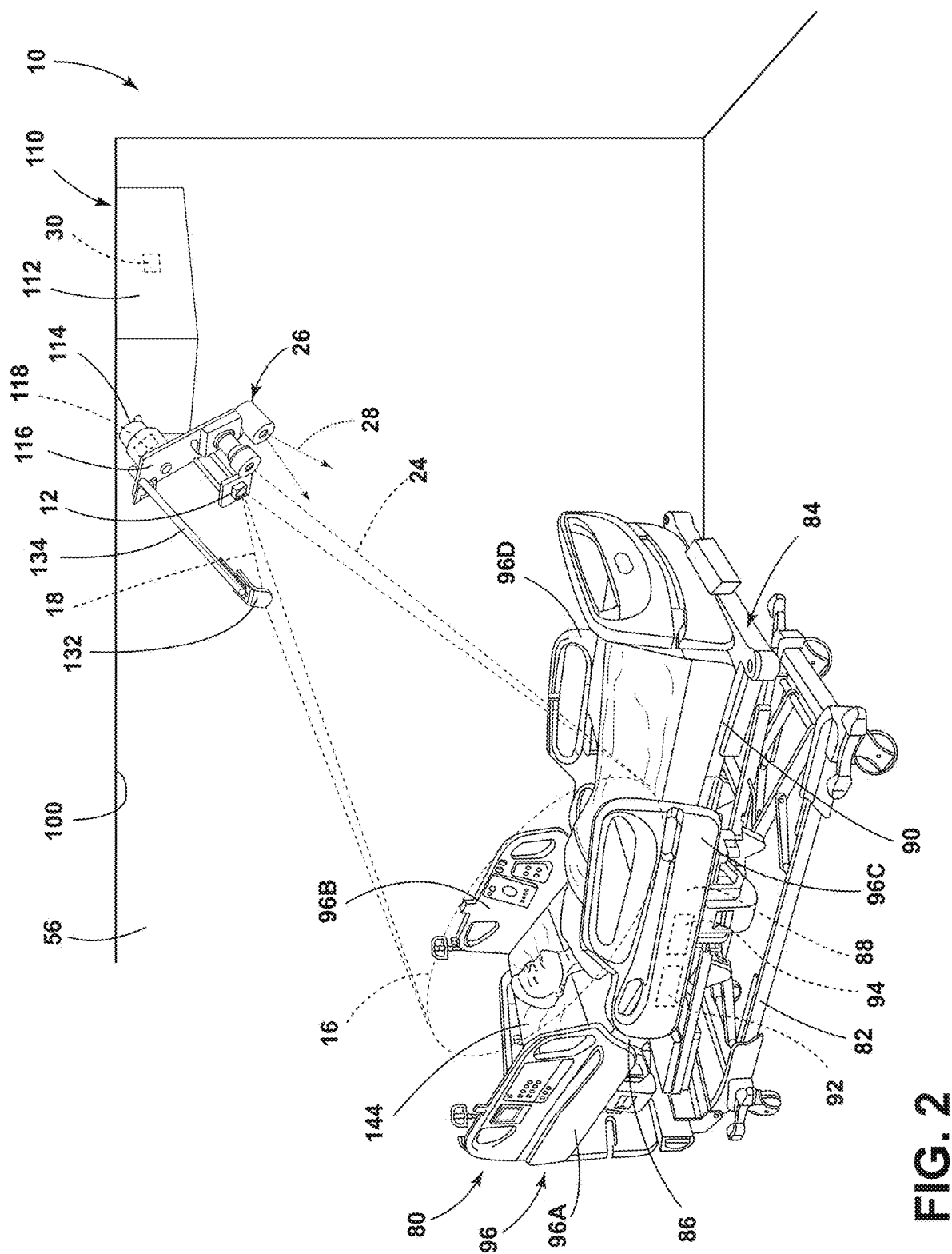
FIG. 2 is a side perspective view of a patient room having a monitoring system, according to the present disclosure.
Figure 3:
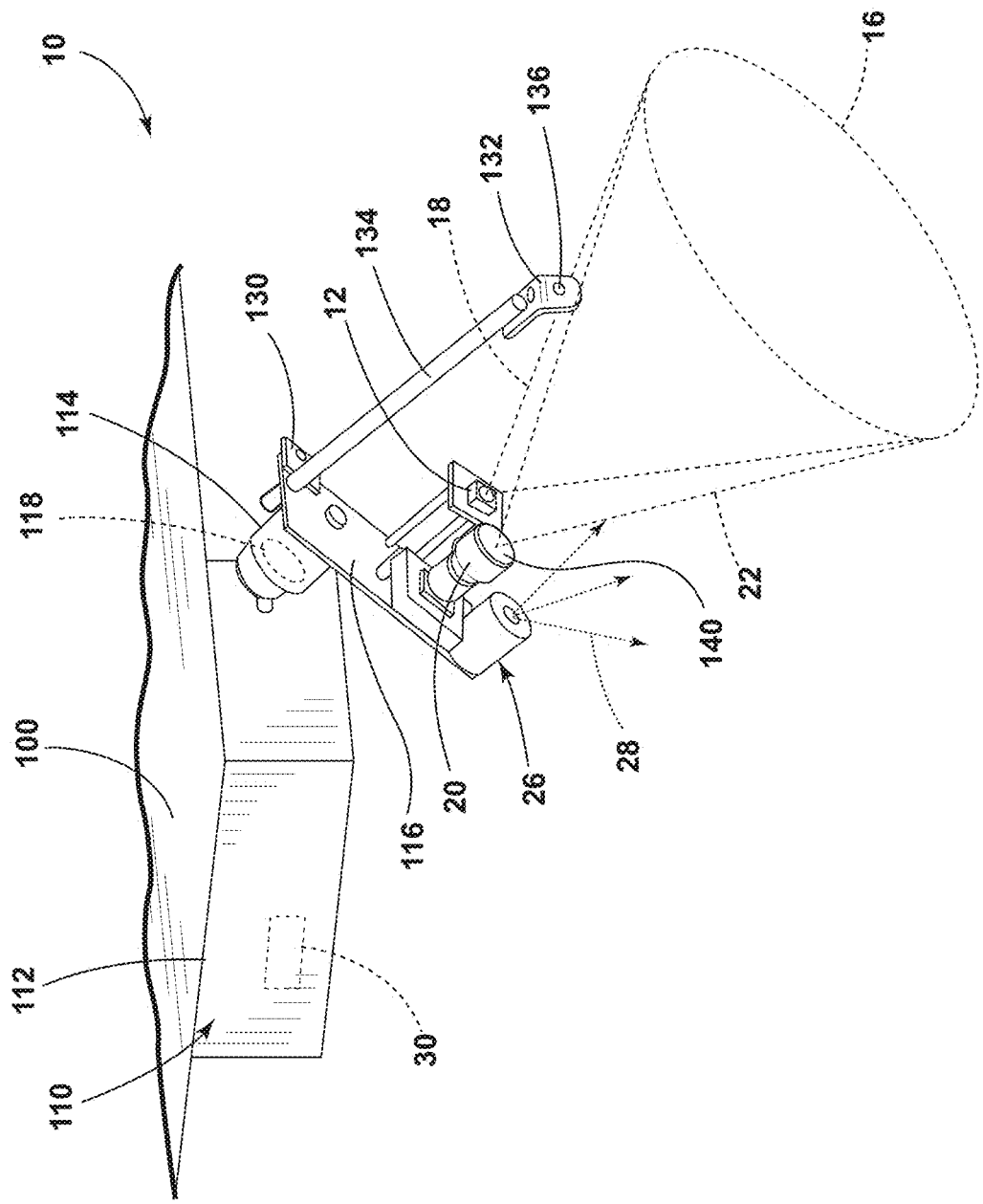
FIG. 3 is a side perspective view of a monitor assembly, according to the present disclosure.

Referring to FIGS. 2 and 3, during the stay at the medical facility 50, caregivers generally monitor the patient, which includes monitoring physical parameters, such as vital signs information 70, and movement of the patient. The vital signs information 70 and movement may be monitored utilizing the monitoring system 10, which may be configured to provide a contactless and continuous method for monitoring the patient. In the example illustrated in FIG. 2, the monitoring system 10 is included in the patient room 56. However, it is contemplated that each room including, for example, patient rooms 56, surgical suites 54, imaging rooms, etc., may utilize the monitoring system 10 to obtain and monitor health information about the patient.

In the illustrated example of the patient room 56 shown in FIGS. 1 and 2, the patient is positioned on a support apparatus 80. The support apparatus 80 is illustrated as a medical bed, but may also be configured as a surgical table, a stretcher, a chair, or other structure for supporting the patient. The support apparatus 80 generally includes a base frame 82 and an upper frame 84 coupled to the base frame 82. The upper frame 84 is adjustable relative to the base frame 82 (e.g., raise, lower, tilt, etc.). Additionally, the upper frame 84 includes multiple segments 86, 88, 90 that are independently adjustable relative to one another, allowing the upper frame 84 to articulate between various positions (e.g., an elevated head region, an elevated foot region, etc.).

The support apparatus 80 generally includes actuation assemblies 92, 94 configured to adjust the position of the upper frame 84. One actuation assembly 92 may adjust the upper frame 84 relative to the base frame 82, while the other actuation assembly 94 may adjust the independent segments 86, 88, 90 of the upper frame 84 relative to one another. The support apparatus 80 also includes siderails 96, which are configured to be raised and lowered to selectively prevent or allow ingress and egress on the support apparatus 80. The support apparatus 80, as illustrated, includes two head siderails 96A, 96B and two base siderails 96C, 96D, collectively referred to herein as the siderails 96. The siderails 96 may be manually adjusted or may be automatically adjusted. Information relating to a position of the support apparatus 80, a position of the siderails 96, and a position of the patient on the support apparatus 80 may be utilized by the monitoring system 10 as described herein.

Referring still to FIGS. 2 and 3, the monitoring system 10 is utilized for determining a variety of information about the patient on the support apparatus 80 via contactless methods. In this way, the monitoring system 10 is spaced from the patient. In the illustrated example, the monitoring system 10 is coupled to a ceiling 100 within the patient room 56. The support apparatus 80 may be positioned in a select location of the patient room 56 to be positioned within the first field of view 18 and the second field of view 24 of the monitoring system 10.

The monitoring system 10 includes a monitor assembly 110 that has a housing 112 coupled to the ceiling 100 in the patient room 56. A connector 114 extends from the housing 112 to a support plate 116. The connector 114 may be stationary, or alternatively, may include an actuator 118 that adjusts a position of the support plate 116 relative to the housing 112.

The monitor assembly 110 includes an ambient temperature sensor 130 coupled to the support plate 116. The ambient temperature sensor 130 is configured to sense an ambient temperature within the patient room 56. The ambient temperature may be utilized by the monitoring system 10 to monitor a condition of the patient room 56, as well as for determining certain vital signs information 70 of the patient.

The monitoring system 10 also includes a reference tab 132, which is spaced from the support plate 116 by an elongated support 134. The reference tab 132 includes a tab temperature sensor 136 configured to sense a temperature of the reference tab 132. The reference tab 132 is utilized as a reference temperature for determining the vital signs information 70 and improving the accuracy of the first imager 12 as described herein. The reference tab 132 extends partially into the first field of view 18 of the first imager 12.

Referring still to FIGS. 2 and 3, the first imager 12 is coupled to the support plate 116. The first imager 12 defines the first field of view 18 that extends away from the monitor assembly 110 and toward the support apparatus 80. The first imager 12 is generally configured as a thermal camera or imager, which is configured to capture thermal imaging (i.e., the first image data 14) within the first field of view 18 by detecting thermal radiation of the patient on the support apparatus 80. In certain aspects, the first imager 12 may be configured as a long wavelength infrared imager (LWIR), which is sensitive to the LWIR spectrum having a wavelength range between about 8 µm and about 14 µm. This is the wavelength range typically emitted by human bodies. In a specific example, the first imager 12 may be a thermal 20K pixel camera module. In another specific example, the first imager 12 may be a FLIP Lepton® Camera Module.

With reference to FIG. 3, the second imager 20 is coupled to the support plate 116 proximate to the first imager 12. The second imager 20 defines the second field of view 24 that extends away from the monitor assembly 110 and toward the support apparatus 80. Generally, the second imager 20 is configured as a monochromatic imager, which is configured to detect electromagnetic energy in a predefined wavelength spectrum and output monochromatic imaging, such as, for example, grayscale imaging (i.e., the second image data 22) captured within the second field of view 24. According to various aspects, the second imager 20 is configured as a near infrared (NIR) camera operating within the NIR light bandwidth, which generally has a wavelength range between about 750 nm and about 2,500 nm. In various examples, the second imager 20 may operate within the NIR light bandwidth having a wavelength range between about 750 nm and about 1,500 nm. Further, the second imager 20 may operate within the NIR light bandwidth having a wavelength range between about 800 nm and about 900 nm. In certain aspects, the second imager 20 may be sensitive to a light bandwidth of about 850 nm.

Additionally, it is contemplated that the second imager 20 may be a charge coupled device (CCD), a complementary metal oxide semiconductor (CMOS) imager, or any type of monochromatic camera. In a specific example, the second imager 20 may include at least one AR0522 CMOS image sensor. In an additional or alternative example, the second imager 20 may be a monochromatic 5M pixel camera module.

Referring again to FIG. 3, the second imager 20 includes a bandwidth filter 140 coupled thereto to filter which wavelength of light is received by the second imager 20. The bandwidth filter 140 generally corresponds with the operating bandwidth range of the second imager 20. Accordingly, the bandwidth filter 140 may allow NIR light having a wavelength in a range between about 750 nm and about 2,500 nm. In various examples, the bandwidth filter 140 may allow NIR light having a wavelength in a range between about 750 nm and about 1,500 nm. Further, the bandwidth filter 140 may allow NIR light having a wavelength in a range between about 800 nm to about 900 nm to be received by the second imager 20.

The first field of view 18 and the second field of view 24 are each directed to and include the target area 16, which encompasses at least a head and chest region of the patient on the support apparatus 80. In this way, the first field of view 18 and the second field of view 24 at least partially overlap, and the target area 16 falls within an intersecting region of the first field of view 18 and the second field of view 24 to be captured by both the first and second imagers 12, 20. Accordingly, each of the first image data 14 and the second image data 22 includes imaging of at least the head and chest regions of the patient.

Typically, the support apparatus 80 is positioned in a select location in the patient room 56 such that an upper body or head portion 144 of the support apparatus 80 is included in the target area 16. It is contemplated that the actuator 118 operably coupled to the connector 114 may adjust the support plate 116, and consequently the first and second imagers 12, 20, to ensure the target area 16 is included in each of the first and second fields of view 18, 24. The caregiver may confirm the alignment between the monitor assembly 110 and the support apparatus 80 via an application interface 150 (FIG. 21) described in detail herein.

Additionally or alternatively, the controller 30 of the monitoring system 10 may be able to determine if an object within the target area 16 is the head portion 144 of the support apparatus 80 and may automatically adjust the support plate 116 to position the head portion 144 of the support apparatus 80 in the target area 16. In such examples, the controller 30 is configured to store dimensions and other information for identifying the support apparatus 80. The controller 30 may also identify the position of the support apparatus 80 related to other features within the patient room 56 and/or based on the associated position within a calibrated coordinate grid and operating envelope of the patient room 56. The operating envelope may be defined or programmed into the controller 30 as a predetermined working range defined in relation to the coordinated grid.

Referring still to FIGS. 2 and 3, the monitor assembly 110 also includes the emitter 26 coupled to the support plate 116. The emitter 26 includes a light source 160 configured to emit the light 28 into an area surrounding the monitor assembly 110 to optimize an image quality of at least the second image data 22. The emitter 26 emits the light 28 into the area surrounding the monitor assembly 110 to provide an adequate intensity for capturing at least the second image data 22.

In various aspects, the light source 160 is a single NIR light emitting diode (LED) or an array of NIR LEDs. Generally, the light 28 emitted by the emitter 26 is within the operating wavelength of the second imager 20. In this instance, the light 28 has a wavelength in a range between about 750 nm and about 2,500 nm. In various examples, the second imager 20 may operate within the NIR light bandwidth having a wavelength range between about 750 nm and about 1,500 nm, and the light 28 emitted by the emitter 26 may have a wavelength in a range between about 750 nm and about 1,500 nm. In additional examples, when the second imager 20 operates within the NIR light bandwidth having a wavelength range between about 800 nm and about 900 nm, the light 28 may have a wavelength in a range from about 800 nm to about 900 nm. It is contemplated that the emitter 26 may continually emit light 28 when the monitoring system 10 is activated to provide illumination for the second imager 20 to continually capture the second image data 22.

The emitter 26 is utilized by the monitoring system 10 to improve the image quality of at least the second image data 22 due to the NIR light 28 being within the operating range of the second imager 20. Moreover, the emitter 26 enables continuous monitoring of the patient during daylight and nighttime conditions. The light 28 emitted from the emitter 26 allows the second imager 20 to capture the second image data 22 regardless of other light conditions within the patient room 56 (e.g., sunlight, nighttime, overhead room light, lamp, etc.).

In certain aspects, multiple emitters 26 may be included in the monitoring system 10. The use of multiple emitters 26 may allow for directing light 28 at different angles toward the support apparatus 80, thereby minimizing a shadowing effect on the patient. A shadowing effect may reduce the quality of at least the second image data 22 being captured by the second imager 20. Moreover, each emitter 26 included in the monitoring system 10 may be operably coupled with an actuator 162. The actuator 162 may adjust the position of the emitter 26 independently of the position of the support plate 116 to emit light 28 in a different direction to assist in reducing the shadowing effect on the patient, while not substantially interfering with the first and second fields of view 18, 24.

Figure 4:
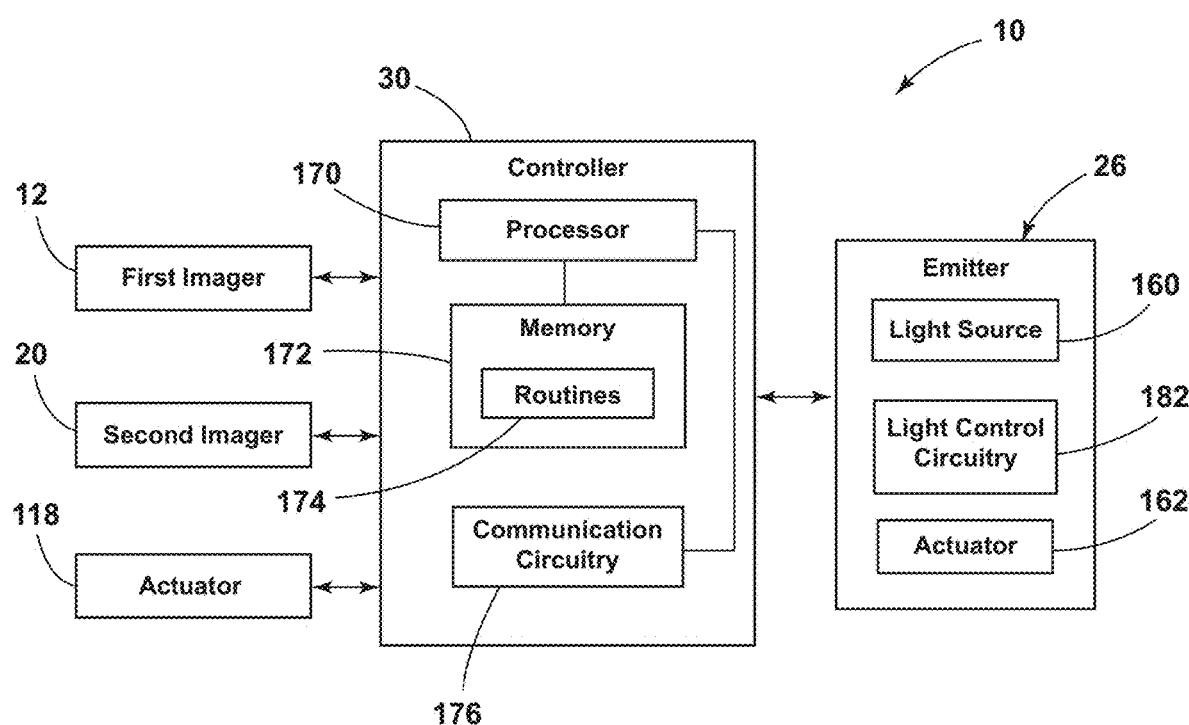
FIG. 4 is a block diagram of a monitoring system, according to the present disclosure.
Figure 18:
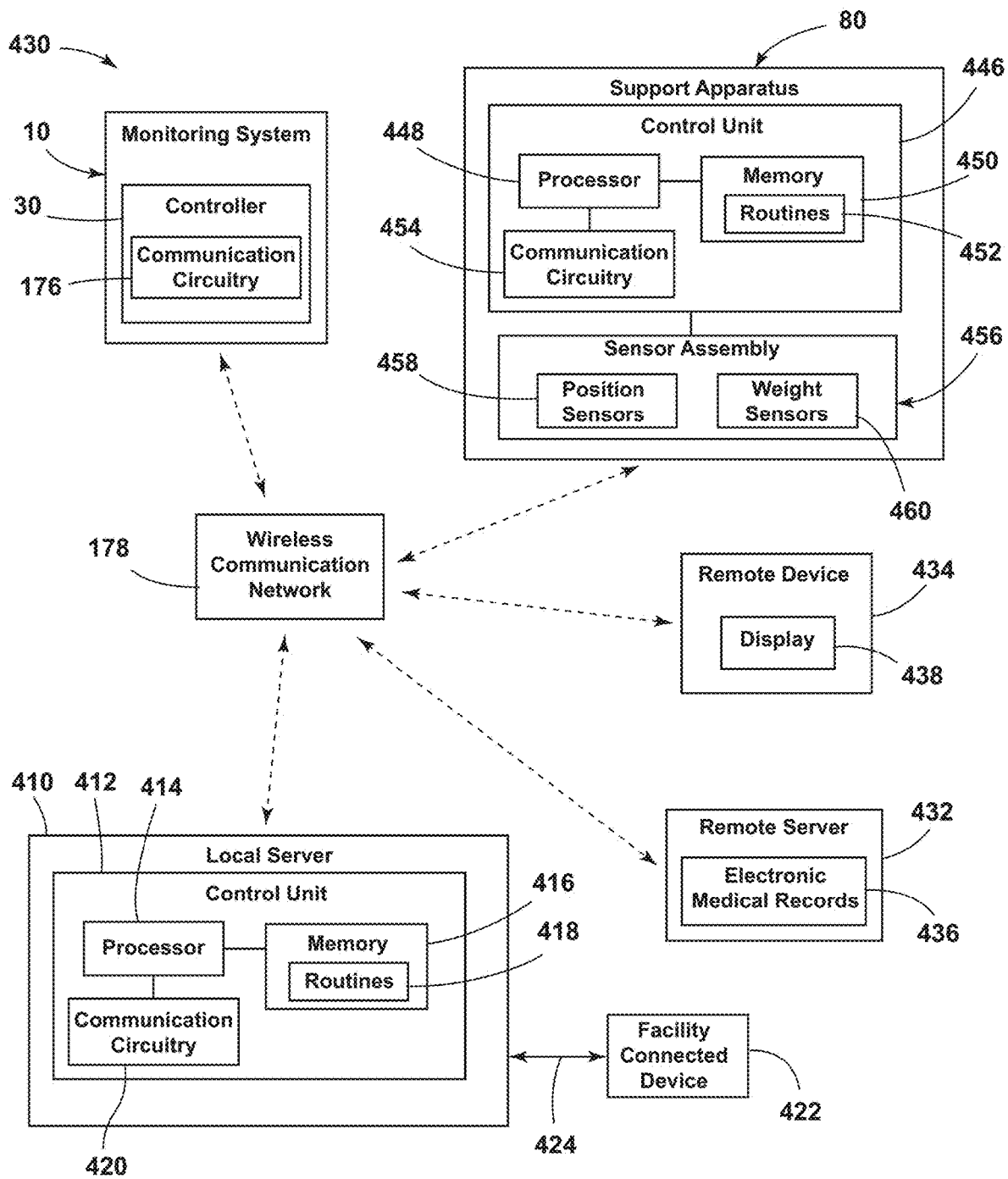
FIG. 18 is a block diagram of an information system of a medical facility, according to the present disclosure.

Referring to FIG. 4, the controller 30 of the monitoring system 10 includes a processor 170, a memory 172, and other control circuitry. Instructions or routines 174 are stored within the memory 172 and executable by the processor 170. The control circuitry includes communication circuitry 176 to allow the controller 30 to communicate via a communication network 178 (FIG. 18).

Each of the first imager 12 and the second imager 20 are communicatively coupled with the controller 30. The controller 30 is configured to selectively and independently activate each of the first and second imagers 12, 20 to begin capturing the first and second image data 14, 22, respectively. The first and second image data 14, 22 is continuously communicated to the controller 30 for processing.

Still referring to FIG. 4, the emitter 26 is also communicatively coupled with the controller 30. The emitter 26 generally includes the light source 160 operably coupled with light control circuitry 182. The controller 30 sends a pulse width modulation signal to the light control circuitry 182 to control the intensity of the light 28 emitted by the light source 160. The controller 30 may also communicate with the actuator 162 of the emitter 26 to change the direction of the emitted light 28.

Figure 5:
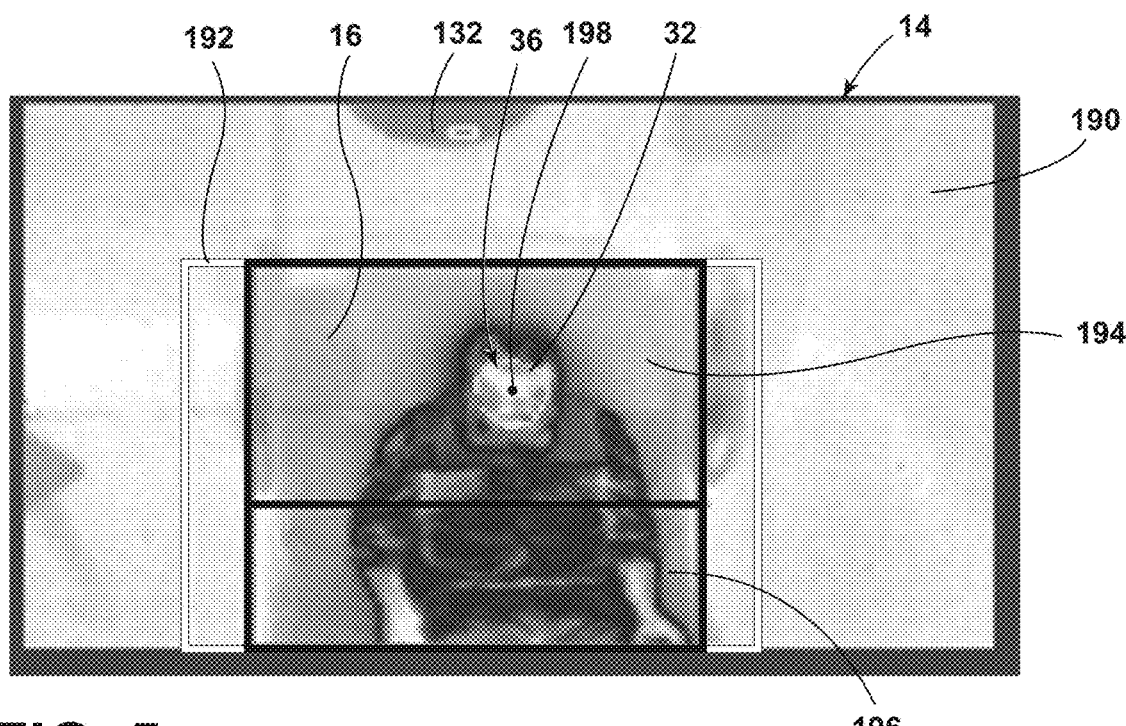
FIG. 5 is a representation of a thermal image frame captured by a thermal camera of a monitoring system, according to the present disclosure.

With reference now to FIG. 4, as well as FIG. 5, the first imager 12 is configured to capture multiple thermal image frames 190, which collectively form the first image data 14. Each thermal image frame 190 is communicated to the controller 30 and may be processed independently. The multiple thermal image frames 190 may also be compared with one another to find patterns or trends within the image data 14. The thermal image frames 190 may be captured at predetermined intervals based on a predefined program or instruction from the controller 30. The first imager 12 generally operates at a frame rate, which defines the number of thermal image frames 190 captured and communicated by the first imager 12 to the controller 30 in a predefined period of time. The frame rate may be, for example, 10 frames per second, 30 frames per second, 60 frames per second, etc.

An example of one thermal image frame 190 is illustrated in FIG. 5. Each thermal image frame 190 is an image of the patient at a single point in time. The thermal image frame 190 shows varying thermal radiations from the patient on the support apparatus 80, with discrete portions of the thermal image frame 190 corresponding to a discrete temperature emitted from the patient. The thermal image frame 190 also includes a depiction of the reference tab 132, which extends into the first field of view 18 of the first imager 12. With the reference tab 132 extending into the thermal image frame 190, the first imager 12 is configured to sense a temperature of the reference tab 132. The reference tab 132 and the tab temperature sensor 136 may be utilized for correcting any error in temperature sensed by the first imager 12 as discussed further herein.

Further, the thermal image frame 190 is processed by the controller 30 to include visual indicators. For example, the controller 30 determines an operating boundary 192 within the thermal image frame 190, which includes at least an upper body of the patient on a portion of the support apparatus 80. The operating boundary 192 may align with an outer periphery of the support apparatus 80, such that, in the illustrated configuration, the operating boundary 192 operates as a bed boundary. The operating boundary 192 coincides with the target area 16 and is utilized to determine regions of interest (ROIs) 194, 196 on the patient. The ROIs 194, 196 define a subset of data in the thermal image frame 190 that is relevant for the purpose of determining vital signs information 70 of the patient as determined by an object recognition routine 174 of the controller 30.

Utilizing the operating boundary 192, the controller 30 determines the first ROI 194, corresponding with a head region or zone of the patient, and the second ROI 196, corresponding with a body or mid-section zone of the patient within the thermal image frame 190. In the illustrated example of FIG. 5, the ROIs 194, 196 are narrower than the operating boundary 192 to remove less relevant image data from being processed. However, the ROIs 194, 196 may have a same or greater width than the operating boundary 192 without departing from the teachings herein. Utilizing the ROIs 194, 196 and thermal radiation from a face of the patient, the controller 30 determines the facial region 32 of the thermal image frame 190 and a selected point, such as a center point 198 of the facial region 32, which is indicative of the head position 36 of the patient. While the operating boundary 192 and ROIs 194, 196 are visually indicated on the thermal image frame 190 illustrated in FIG. 5, it is contemplated that the controller 30 may process the thermal image frame 190 without visibly manipulating the first image data 14.

Figure 6:
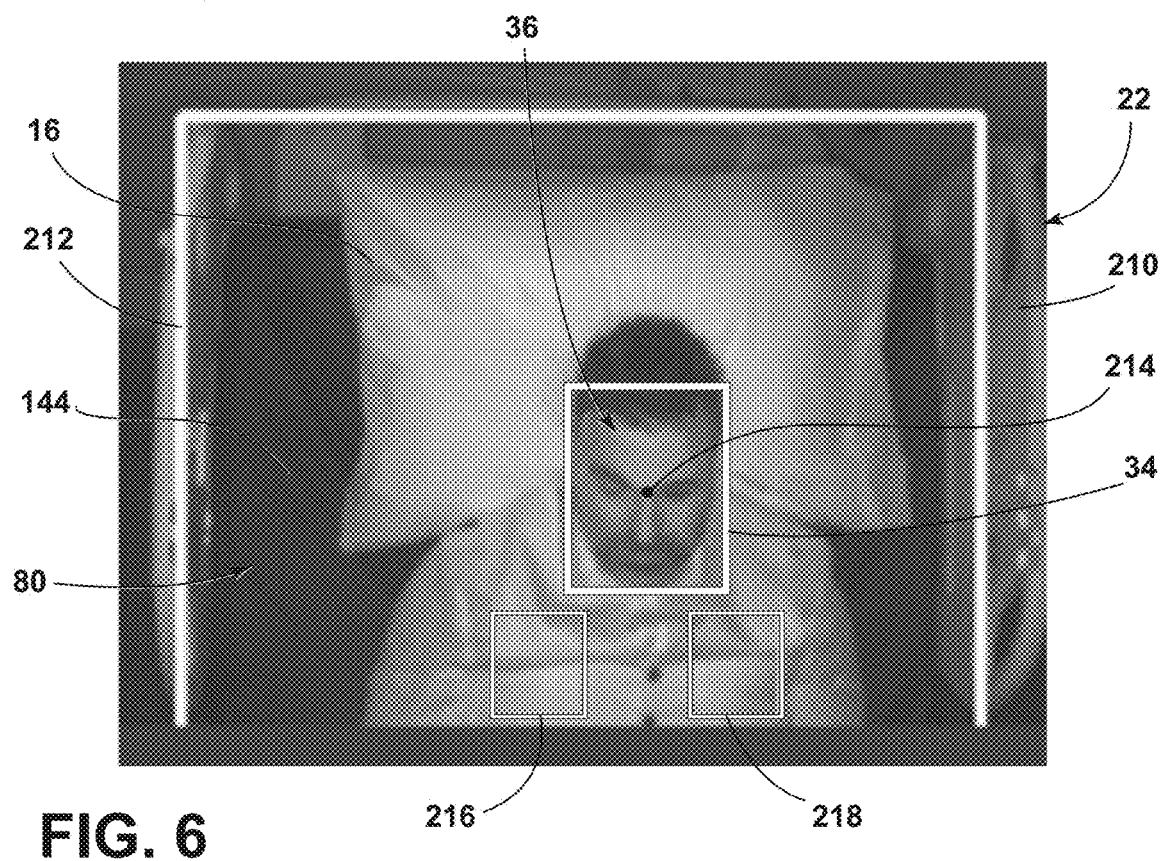
FIG. 6 is a representation of a grayscale image frame captured by a monochromatic camera of a monitoring system, according to the present disclosure.

Referring still to FIG. 4, as well as FIG. 6, the second imager 20 is configured to capture multiple grayscale image frames 210 or other monochromatic image frames 210. Each grayscale image frame 210 may be independently communicated and processed by the controller 30. The multiple grayscale image frames 210 may also be compared with one another to find patterns or trends within the image data 22. The grayscale image frames 210 may be captured at predetermined intervals based on a predefined program or instruction from the controller 30. The second imager 20 generally operates at a frame rate, which defines the number of grayscale image frames 210 communicated by the second imager 20 to the controller 30 in a predefined period of time. The frame rate may be, for example, 10 frames per second, 30 frames per second, 60 frames per second, etc. The frame rate of the second imager 20 is adjustable by the controller 30 as discussed herein.

An example grayscale image frame 210 is illustrated in FIG. 6. Each grayscale image frame 210 is an image of the patient at a single point in time. The controller 30 processes the grayscale image frame 210 to include multiple visual indicators. The controller 30 determines an operating boundary 212, which coincides with the target area 16. The operating boundary 212 may operate as a bed boundary, extending along a periphery of the support apparatus 80. Using the thermal image frame 190, the controller 30 determines a selected point, such as a central point 214 on the grayscale image frame 210 that corresponds with the center point 198 on the thermal image frame 190. The central point 214 is also indicative of the head position 36 of the patient. The controller 30, utilizing the central point 214, determines the facial ROI 34 and two chest ROIs 216, 218. The ROIs 34, 216, 218 define a subset of data in the grayscale image frame 210 that is determined by the object recognition routine 174 and/or an image processing routine 174 of the controller 30 to be relevant to determining the vital signs information 70 of the patient. It is contemplated that the operating boundary 212 and ROIs 34, 216, 218 may not be visible, such that the controller 30 processes the grayscale image frame 210 without visibly manipulating the second image data 22.

Figure 7:
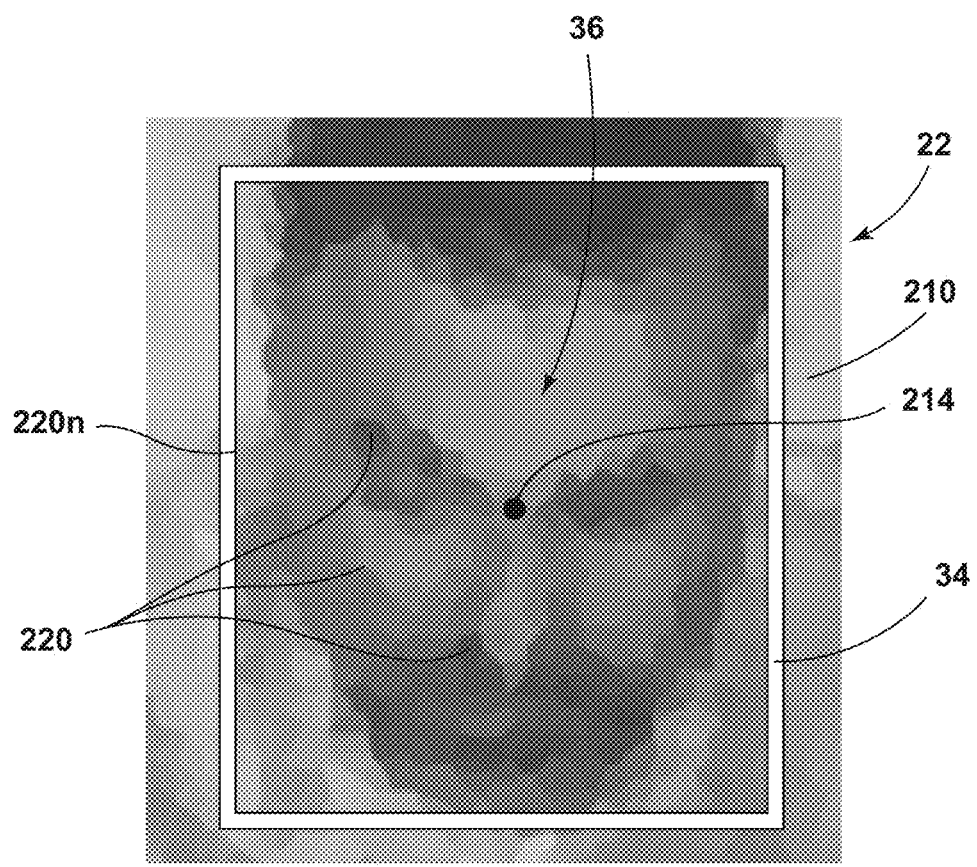
FIG. 7 is an enlarged view of a facial region of interest in a grayscale image frame captured by a monitoring system, wherein the facial region of interest includes a plurality of pixels, according to the present disclosure.

Referring to FIG. 7, the facial ROI 34 of the grayscale image frame 210 is illustrated in isolation from a remainder of the grayscale image frame 210. The grayscale image frame 210 is comprised of pixels 220 and the facial ROI 34 includes a total number of pixels $220n$. Each pixel 220 has a pixel value, which describes a brightness and/or color that corresponds with the pixel 220. For grayscale images, each pixel 220 has a single pixel value (i.e., a single local pixel value) that corresponds to the brightness of the pixel 220, and the single pixel value generally ranges from about zero, which corresponds to black, to about 255, which corresponds to white. The controller 30 utilizes the pixels 220 of the facial ROI 34 to determine the vital signs information 70 as described in detail herein.

Figure 8:
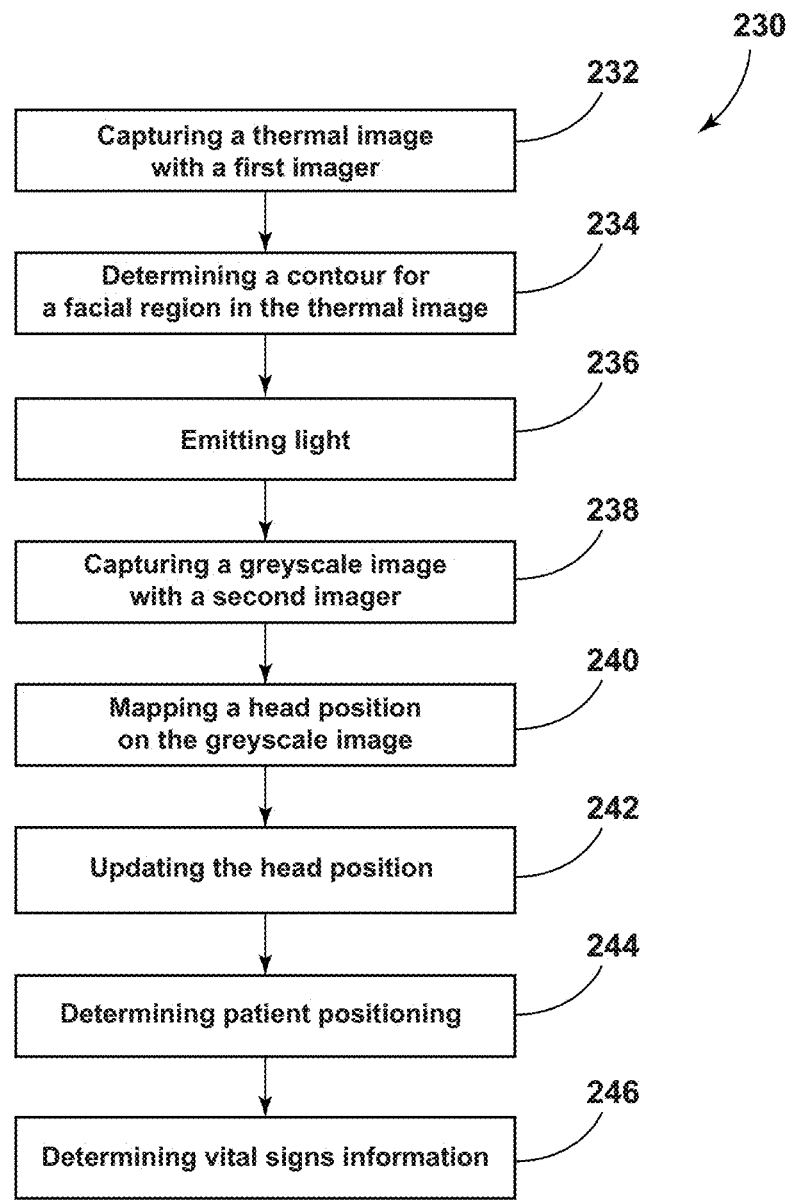
FIG. 8 is a flow diagram of a method of determining patient vital signs information, according to the present disclosure.

Referring to FIG. 8, as well as FIGS. 1-7, the monitoring system 10 provides for remote monitoring of the vital signs information 70 of patients, which can be accomplished through a dual imager or dual camera system. The dual imager system allows for contactless monitoring 24/7 once the monitoring system 10 is activated. The contactless monitoring contributes to the safety and comfort of the patient, as well as assists with clinical workflow. For example, the patient may not have to wear a device that monitors certain vital signs. Use of these devices can result in the development of pressure injuries or discomfort. Additionally, a caregiver may view the vital signs information 70 from a separate location in the medical facility 50, saving time from having to physically obtain the vital signs information 70 from the patient room 56. Each of the first imager 12 and the second imager 20 may continuously send the image data 14, 22 to the controller 30 to be processed at the specific frame rates, allowing continuous monitoring of the patient.

The monitoring system 10 performs a method 230 of monitoring a patient, including positioning information and vital signs information 70 of the patient. The method 230 includes step 232 of capturing the thermal image frame 190 (i.e., the first image data 14) with the first imager 12. The thermal image frame 190 is communicated to the controller 30 for processing. In step 234, the controller 30 determines the operating boundary 192 within the thermal image frame 190, which coincides with the target area 16 and is utilized to determine the ROIs 194, 196. The controller 30 determines a contour on the facial region 32 of the thermal image frame 190 within the first ROI 194. The facial thermal radiation enables efficient location of the facial region 32 of the patient in the thermal image frame 190. Utilizing the facial region 32 on the thermal image frame 190, the controller 30 determines the center point 198 of the facial region 32. The controller 30 determines at least one coordinate of the center point 198, which is representative of the head position 36. In various examples, the controller 30 determines x- and y-coordinates of the center point 198 within the thermal image frame 190 as described further herein. In step 234, the controller 30 may also manipulate the first image data 14 to include the visual indicators of the operating boundary 192, the ROIs 194, 196, and the center point 198.

In step 236, the controller 30 activates the emitter 26 to emit the NIR light 28 into the area surrounding the monitor assembly 110. In step 238, the grayscale image frame 210 (i.e., the second image data 22) is captured by the second imager 20 and communicated to the controller 30 for processing. The emission of the NIR light 28 provides adequate illumination for the second image data 22 to be captured. Additionally, in step 238 the controller 30 determines the operating boundary 212 within the grayscale image frame 210.

In step 240, the controller 30 maps the central point 214 on the grayscale image frame 210, which corresponds with the center point 198 on the thermal image frame 190. The central point 214 may be mapped onto the grayscale image frame 210 utilizing geometric transformation. Geometric transformation may be utilized to scale or adjust coordinates of the thermal image frame 190 with coordinates of the grayscale image frame 210 to align the center point 198 of the facial region 32 from the thermal image frame 190 with the central point 214 on the grayscale image frame 210. The controller 30 may also utilize the operating boundaries 192, 212 and common pixels 220 within the operating boundaries 192, 212 to map the central point 214.

Additionally, in step 240, using the central point 214 of the grayscale image frame 210, the controller 30 determines the facial ROI 34, illustrated as a rectangle around the face of the patient in the grayscale image frame 210. It is contemplated that the facial ROI 34 may be an irregular shape or another geometric shape extending over the face of the patient. The controller 30 may also determine two chest ROIs 216, 218 utilizing the coordinates of the central point 214 on the grayscale image frame 210. The first chest ROI 216 is positioned over one side of the chest of the patient, and the second chest ROI 218 is positioned over an opposing side of the chest of the patient. In step 240, the controller 30 may also manipulate the second image data 22 to include the visual indicators of the operating boundary 212, the ROIs 34, 216, 218, and the central point 214.

In step 242, the monitoring system 10 confirms and updates the head position 36 in response to the movement of the patient. As the patient moves on the support apparatus 80, the head position 36 of the patient changes. The head position 36 is confirmed and updated at predefined intervals. Updating the head position 36 is advantageous for increasing the accuracy of the vital signs information 70, as well as for monitoring the position of the patient on the support apparatus 80. The head position 36, including the center point 198 on the thermal image frame 190 and the central point 214 on the grayscale image frame 210, is utilized to determine the various ROIs within the image data 14, 22 for monitoring the patient. Accordingly, updating the head position 36 provides increased accuracy in the vital signs information 70.

In step 244, the monitoring system 10 determines the position of the patient using the head position 36. The monitoring system 10 tracks the movement of the patient by determining changes in the head position 36. The monitoring system 10 utilizes at least one of the first and second image data 14, 22 within the operating boundaries 192, 212, respectively, to determine if the patient is sitting, out of bed, supine, etc.

In step 246, the monitoring system 10 determines the vital signs information 70 of the patient. In various aspects, the vital signs information 70 includes, but is not limited to, a heart rate, a respiration rate, and a facial temperature. The vital signs information 70 may be determined by comparing the pixel value of the pixels 220 within the facial region 32 in the thermal image frame 190, in the facial ROI 34 in the grayscale image frame 210, and/or the chest ROIs 216, 218 in the grayscale image frame 210. Further, the controller 30 may use multiple grayscale image frames 210 captured by the second imager 20 to determine the vital signs information 70 and a change in vital signs information 70 over a period of time. Additionally, in step 246, the controller 30 may be configured to communicate the vital signs information 70 to the caregiver. The controller 30 may also be configured to generate an alert relating to the vital signs information 70 when the vital signs information 70 or a change in the vital signs information 70 is outside a predefined range or a predefined change range, respectively.

Figure 9:
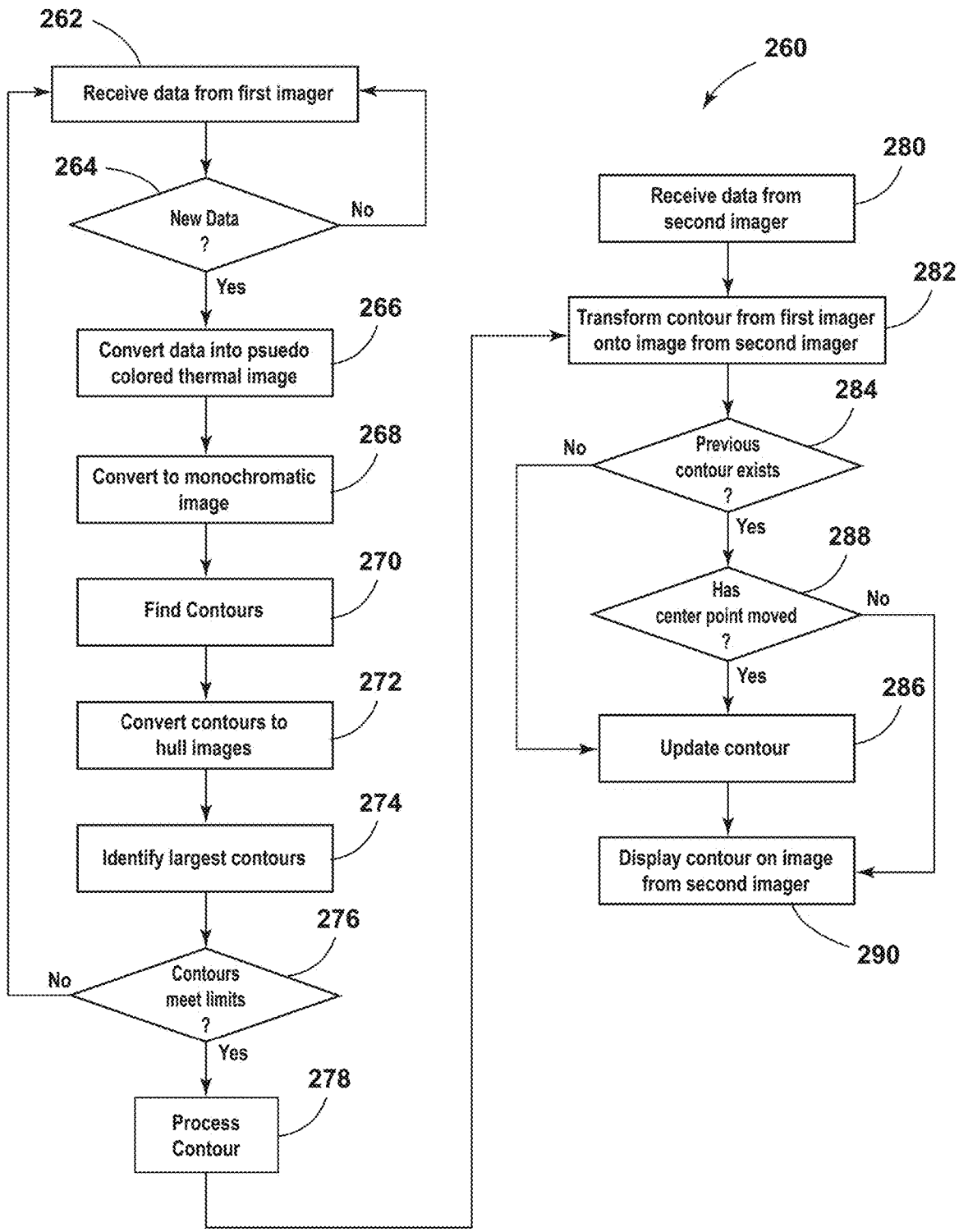
FIG. 9 is a flow diagram of a method of acquiring and processing image data in a monitoring system, according to the present disclosure.

Referring to FIGS. 8 and 9, step 240 of method 230 of identifying and mapping the facial ROI 34 on the grayscale image frame 210 may be accomplished via at least one routine 260, included in routines 174 of the controller 30, directed to image acquisition and processing. In step 262 of the routine 260, the controller 30 receives the thermal image frame 190. In decision step 264, the controller 30 determines whether the thermal image frame 190 is new data. If not, and the thermal image frame 190 was previously processed, the controller 30 returns to step 262 to receive a new thermal image frame 190 to process.

Additionally, in step 264, the controller 30 may utilize the reference tab 132 to correct any temperature errors of the first imager 12. The reference tab 132 extends into the first field of view 18 and is included in the thermal image frame 190. The tab temperature sensor 136 communicates a sensed reference tab temperature to the controller 30. The sensed temperature is configured to be compared to the temperature captured by the first imager 12 within the thermal image frame 190 and is utilized to correct any temperature error in the detected temperature obtained within the first image data 14. It is contemplated that the ambient temperature may also be used to calibrate the first imager 12. If any calibration or correction occurs, the routine 260 may return to step 262 to receive a new thermal image frame 190 for processing.

Returning to decision step 264, if the thermal image frame 190 is new image data, the controller 30 proceeds to step 266 where the first image data 14 received from the first imager 12 is converted into a pseudo colored thermal image. Generally, thermal images are monochromatic images. The monochromatic thermal image frame 190 may be converted to a pseudo thermal image by normalizing the image data and applying a color map. The pseudo thermal image may be advantageous for further differentiating the detected thermal radiations depicted in the thermal image frame 190.

In step 268, the controller 30 creates a converted thermal image frame 190 where the thermal image frame 190 from step 266 is converted into a monochromatic image. Adjusting the thermal image frame 190 from the original monochromatic image, to a pseudo colored thermal image, and to a new monochromatic image may enhance the contrast between different detected thermal radiations. The new monochromatic image may also be advantageous for processing pixel values as described further herein. In converting the thermal image frame 190, pixels of the thermal image frame 190 with data values closest to a predefined maximum data value are white and the other pixels are black. The predefined maximum data value may be stored within the controller 30.

In step 270, the controller 30 analyzes the converted thermal image frame 190 to find contours. A contour is generally an outline that represents the shape or form of an object. The controller 30 includes at least one routine 174 directed to contour detection and attempting to extract curves representing object shapes from the first image data 14 received from the first imager 12. The contours may be detected through intensity differences in the pixels within the monochromatic image from step 268.

In step 272, the controller 30 converts the contours into convex hull shapes, which simplifies the thermal image frame 190 for processing. Generally, convex hull shapes are the smallest convex set that contains a subset, which is typically the contour. In step 274, the controller 30 analyzes the convex hull shapes to identify the largest contour. Typically, the controller 30 processes the head portion 144 of the support apparatus 80 first. If the contours are not identified in the upper portion, the controller 30 processes a lower portion of the support apparatus 80 within the operating boundary 192.

Once a contour is identified, in decision step 276, the controller 30 determines whether the identified contour meets predefined limits. The predefined limits are generally hard-coded maximum and minimum size criteria stored within the controller 30. If the identified contour does not meet the predefined limits, the controller 30 returns to step 262 to receive a new thermal image frame 190. Returning to decision step 276, if the identified contour falls within the predefined limit (i.e., within the hard-coded maximum and minimum size criteria), the controller 30 proceeds to step 278 to process the identified contour. The identified contour generally aligns with the facial region 32 (i.e., a thermal facial contour) as the facial thermal radiation often provides the largest contour.

In step 280, the controller 30 receives the grayscale image frame 210 from the second imager 20. In step 282, the controller 30 utilizes the grayscale image frame 210 from step 280 and the processed contour from step 278 to transform the contour from the thermal image frame 190 onto the grayscale image frame 210. The controller 30 identifies coordinates in each of the thermal image frame 190 and the grayscale image frame 210. The controller 30 then transforms the identified contour from the coordinates identified in the thermal image frame 190 onto the coordinates of the grayscale image frame 210. The contour generally includes the central point 214 and the facial ROI 34 (e.g., the rectangular visual identifier) mapped onto the grayscale image frame 210.

The transformation is accomplished by scaling the identified contour. Generally, the scaling is accomplished by a ratio of a resolution of the second imager 20 divided by a resolution of the first imager 12 and shifting each point by Cartesian X and Y offsets, which are determined by common pixels 220 within an intersecting area of the fields of view. It is contemplated that the controller 30 may include one or more routines 174 for utilizing geometric transformations to transform the contour from the thermal image frame 190 onto the grayscale image frame 210.

In decision step 284, the controller 30 processes the transformed data and determines whether a previous contour exists in the coordinates on the grayscale image frame 210. If the previous contour does not exist, the controller 30 proceeds to step 286 to add or update the contour on the grayscale image frame 210. Once updated, the controller 30 proceeds to step 288 of displaying the contour on the grayscale image frame 210.

Returning to decision step 284, if the previous contour does exist within the coordinates, the controller 30 proceeds to step 290 to determine whether a coordinate of the center point 198 of the identified contour (e.g., the facial region 32) on the thermal image frame 190 has moved by a predefined number of pixels. If the coordinate of the center point 198 has moved by the predefined number of pixels, the controller 30 proceeds to step 286 of updating the contour on the grayscale image frame 210. Accordingly, if the patient moved, thereby moving the center point 198, the grayscale image frame 210 may be updated and remapped with each movement of the patient. Returning to decision step 284, if the coordinate of the center point 198 has not moved by the predefined number of pixels, the controller 30 proceeds to display the previous contour on the grayscale image frame 210 in step 288.

Figure 10:
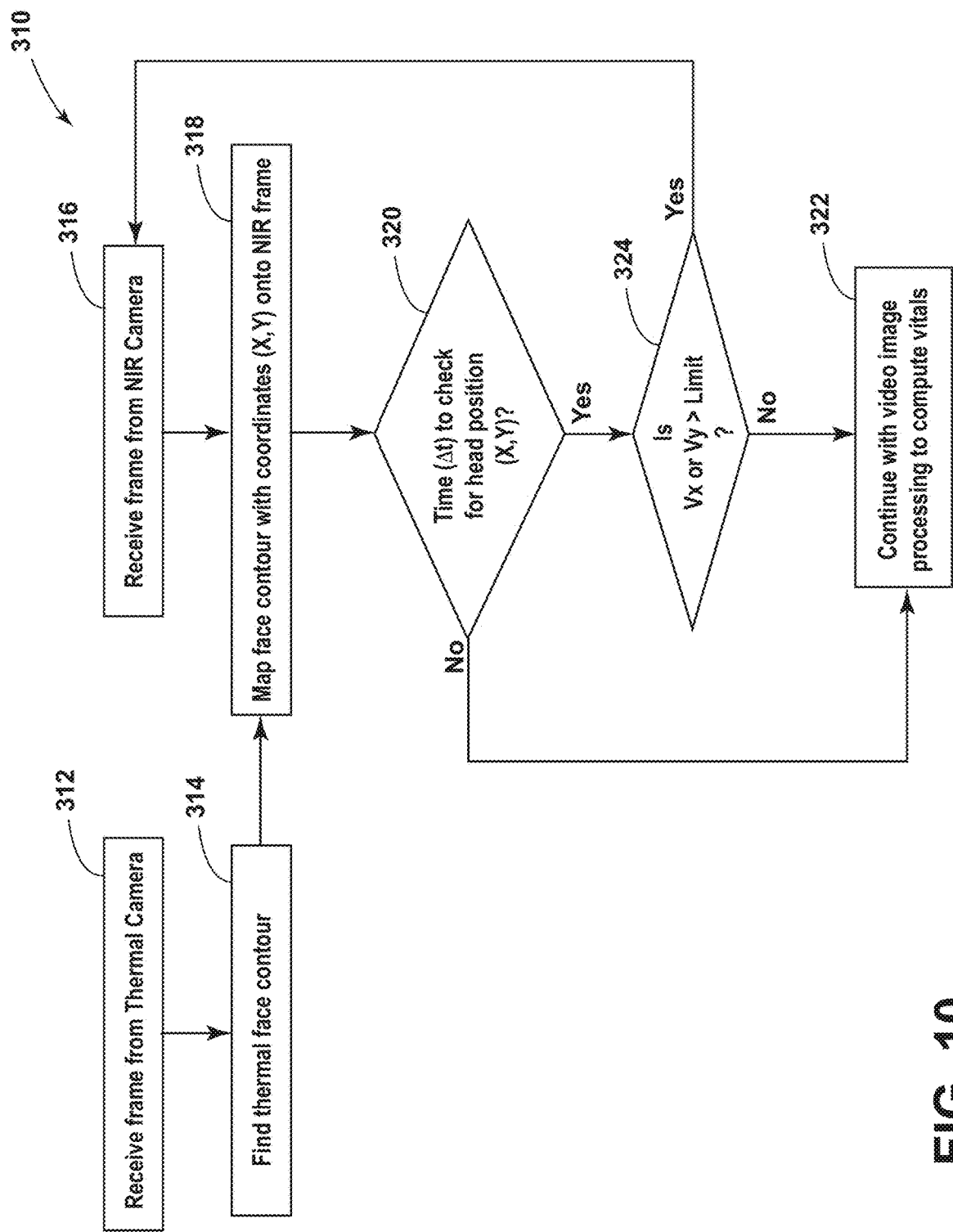
FIG. 10 is a flow diagram of a method of monitoring patient movement within a monitoring system, according to the present disclosure.
Figure 11:
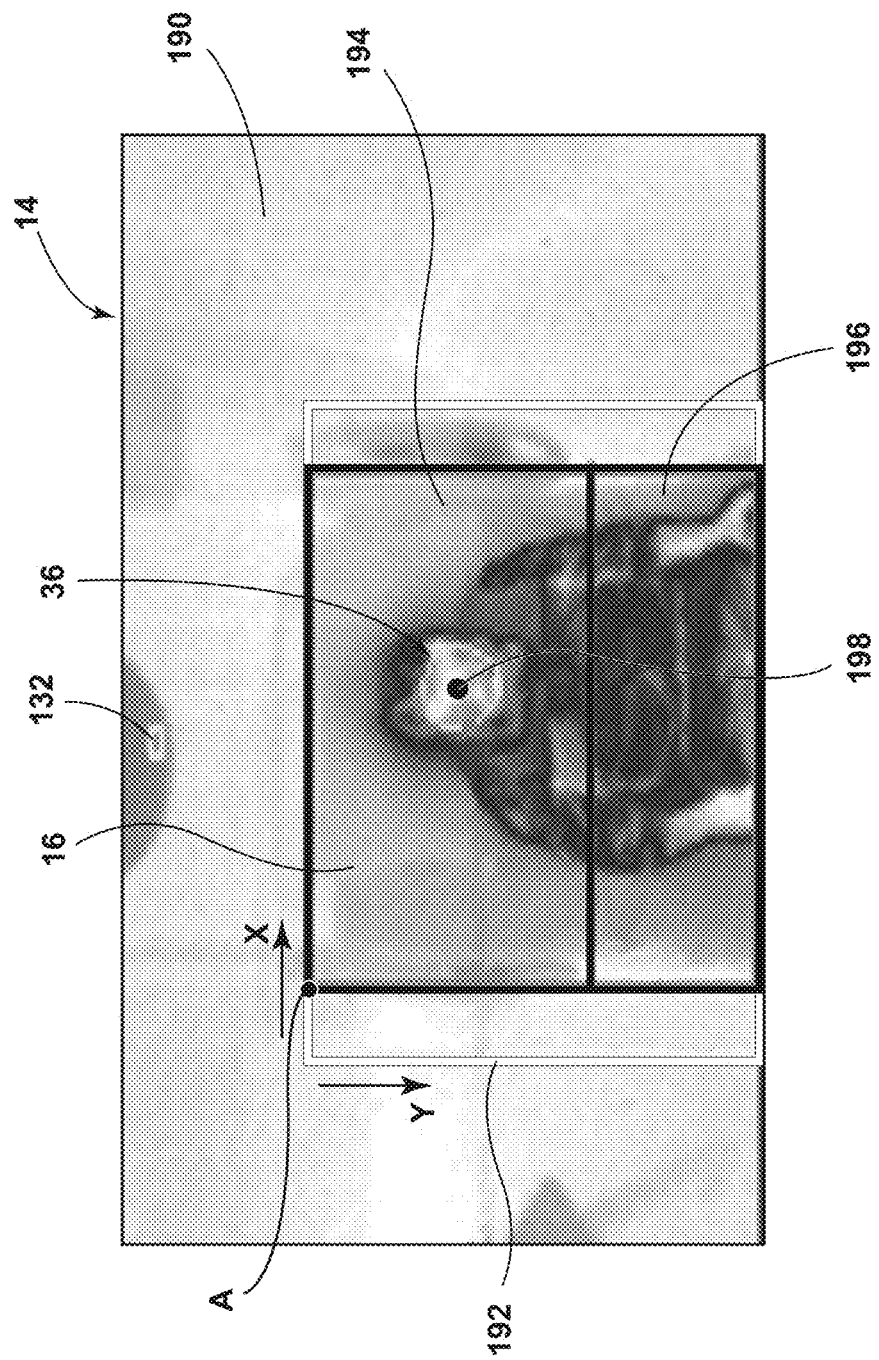
FIG. 11 is a representation of a grayscale image frame captured by a monochromatic camera of a monitoring system indicating a grid for monitoring movement of a patient, according to the present disclosure.

With reference again to FIG. 8, as well as to FIGS. 10 and 11, in step 242 of method 230, the monitoring system 10 is configured to update and confirm the head position 36 of the patient in at least the first image data 14 and the second image data 22. The controller 30 includes at least one movement tracking routine 310, included in routines 174, for confirming and updating the head position 36 of the patient. The movement tracking routine 310 may be accomplished independently of the image acquisition routine 260 in FIG. 9, and therefore may include several overlapping steps directed to image data processing. Alternatively, the movement tracking routine 310 may be performed concurrently with or immediately after the image acquisition routine 260 illustrated in FIG. 9, in which overlapping or repeated steps may be omitted. Updating the information about the head position 36 may be advantageous for improving the accuracy of the vital signs information 70 determined by the monitoring system 10.

Referring still to FIGS. 8-11, the monitoring system 10 includes the movement tracking routine 310, which may be used as a validation process with respect to head movement. The mobility computation allows the monitoring system 10 to determine whether the head of the patient is at rest, in the supine or side position, before processing the image data 14, 22 to determine the vital signs information 70. The validation process may improve the accuracy of the vital signs information 70.

In step 312 of the routine 310, the controller 30 receives the thermal image frame 190 (e.g., the first image data 14) captured by the first imager 12. In step 314, the controller 30 is configured to process the thermal image frame 190 to identify the contour that corresponds with the facial region 32, similar to the routine 260 described in relation to FIG. 9. In step 316, the controller 30 receives the grayscale image frame 210 (i.e., the second image data 22) captured by the second imager 20.

Utilizing the processed thermal image frame 190 and the grayscale image frame 210, the routine 310 proceeds to step 318 where the controller 30 processes the grayscale image frame 210 to map the facial contour from the thermal image frame 190 onto the grayscale image frame 210, which may be similar to the process described in relation to FIG. 9. The facial ROI 34 is generally the area on the grayscale image frame 210 that encompasses the face of the patient. Additionally or alternatively, in step 318, the controller 30 maps the center point 198 on the thermal image frame 190 using coordinates. The controller 30 assigns a grid to the thermal image frame 190 having a first axis in a first direction and a second axis in a second direction, generally perpendicular to the first axis. The grid is defined within the operating boundary 192. Typically, the first axis is an x-axis and the second axis is a y-axis, allowing the controller 30 to define x-coordinates and y-coordinates of features within the thermal image frame 190. Using the x- and y-axes, the controller 30 defines an origin position A where both of the x- and y-coordinates equal zero (i.e., (0, 0)). In the illustrated example of FIG. 11, the origin position A is defined in an upper, left corner of the head rest zone within the operating boundary 192. The head position 36 may then be determined using the x-coordinate and the y-coordinate of the center point 198 relative to the origin position A.

After determining the coordinates on the thermal image frame 190, the coordinates are mapped onto the grayscale image frame 210. The coordinate grid from the thermal image frame 190 is generally mapped onto the grayscale image frame 210 within the operating boundary 212. Transformation may be utilized to align the two grids. The central point 214 is then mapped at the same coordinate as the center point 198 on the thermal image frame 190. The controller 30 determines the facial ROI 34 on the grayscale image frame 210 utilizing the mapped central point 214.

In decision step 320, the controller determines whether a predefined period of time, t, has elapsed (i.e., Δt). The predefined period of time is an interval of time since that last determination of the x- and y-coordinates. The period of time t reflects the frequency at which the monitoring system 10 determines the head position 36 using the coordinates. The period of time may be any practicable period of time, for example, every second. In this way, the current x- and y-coordinates are confirmed or updated at predefined intervals. If a current elapsed time is less than the predefined period of time t (i.e., the predefined period of time has not elapsed), the controller 30 proceeds to step 322 to determine the vital signs information 70 as described further herein.

Returning to decision step 320, if the current elapsed time is equal to or greater than the predefined period of time t (i.e., the predefined period of time has elapsed), the controller proceeds to decision step 324. In decision step 324, the controller determines whether a rate of change in the x-coordinate $V_x$ or a rate of change in the y-coordinate $V_y$ over the change in time exceeds a predefined movement threshold or limit. The predefined limit may be stored within the controller 30 and may be adjustable. The rate of change in the x-coordinate $V_x$ is generally determined as $V_x = \Delta X/\Delta t$, while the rate of change in the y-coordinate $V_y$ is generally determined as $V_y = \Delta X/\Delta t$. The controller 30 is configured to determine if the center point 198 in the thermal image frame 190, and consequently the central point 214 in the grayscale image frame 210, moves in at least one direction (i.e., the x-direction and/or the y-direction in the mapped grid) greater than a predefined threshold over the interval between the current position determination and a previous position determination.

If either $V_x$ or $V_y$ exceeds a predefined limit or a predefined limit range, then the controller returns to step 316 to receive a subsequent or new grayscale image frame 210. It is also contemplated that the controller 30 may return to step 312 to receive a subsequent or new thermal image frame 190 in addition to or instead of the grayscale image frame 210. Each of the center point 198 on the thermal image frame 190 and the central point 214 of the grayscale image frame 210 are continuously remapped with head movement. Obtaining new image data 14, 22 when the head position 36 has moved more than a predefined limit in either the x-direction or the y-direction is advantageous for increasing accuracy of the monitoring system 10, as well as tracking the position of the patient.

Returning to decision step 324, if both the rate of change in the x-coordinate $V_x$ and the rate of change in the y-coordinate $V_y$ are below or less than the predefined threshold or limit, the controller 30 proceeds to step 322 to determine physical parameters of the patient. The physical parameters may include the patient positioning and/or the vital signs information 70.

The monitoring system 10 may track the center point 198 within the operating boundary 192 across thermal image frames 190 captured as the first image data 14. In tracking the center point 198, the monitoring system 10 is configured to track the position of the patient. For example, using the coordinates of the center point 198, the monitoring system 10 is configured to determine whether the patient is sitting, supine, out of bed, or in various other positions.

Figure 12:
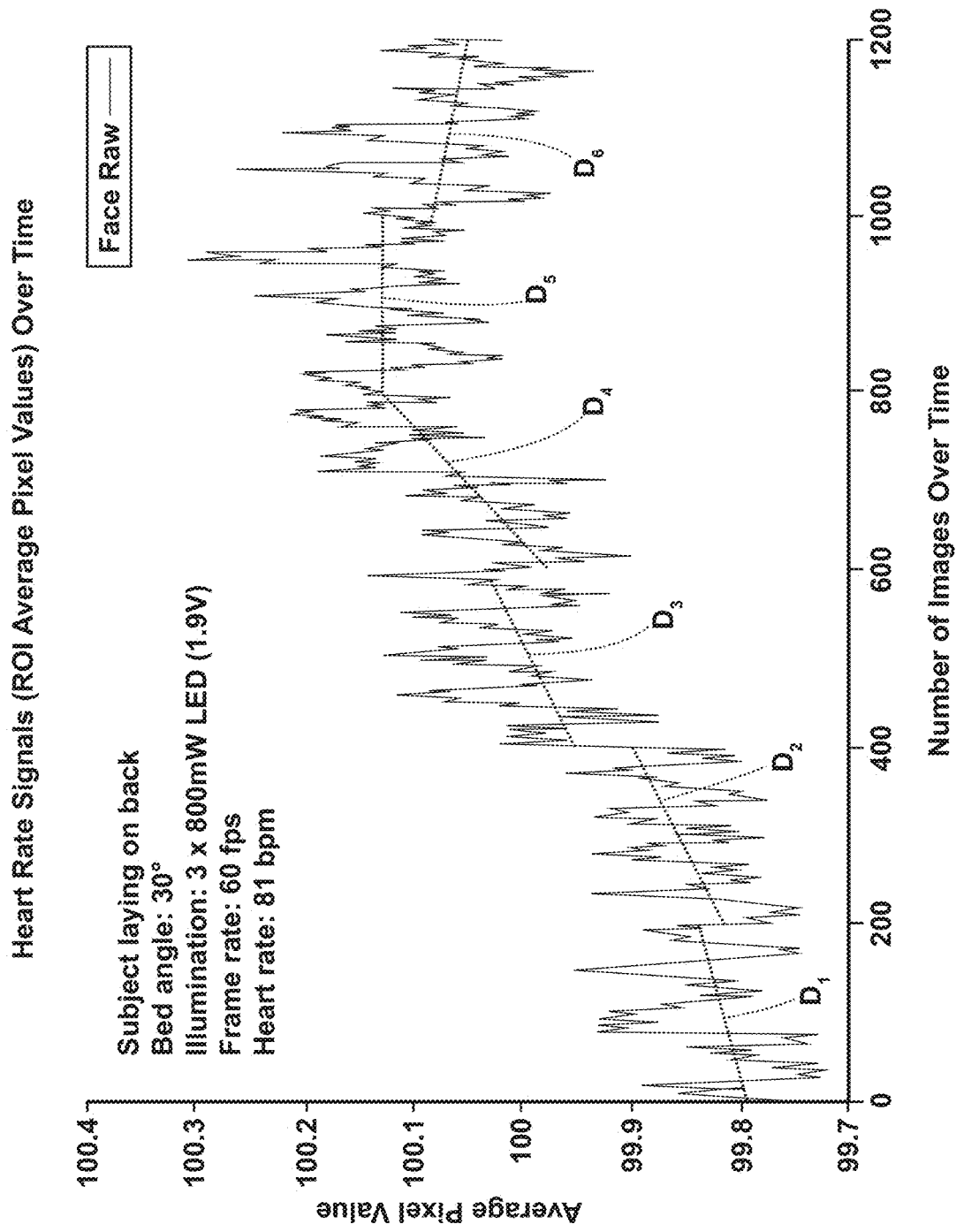
FIG. 12 is a graph of average pixel value compared to the number of images over time to determine a heart rate, according to the present disclosure.
Figure 13:
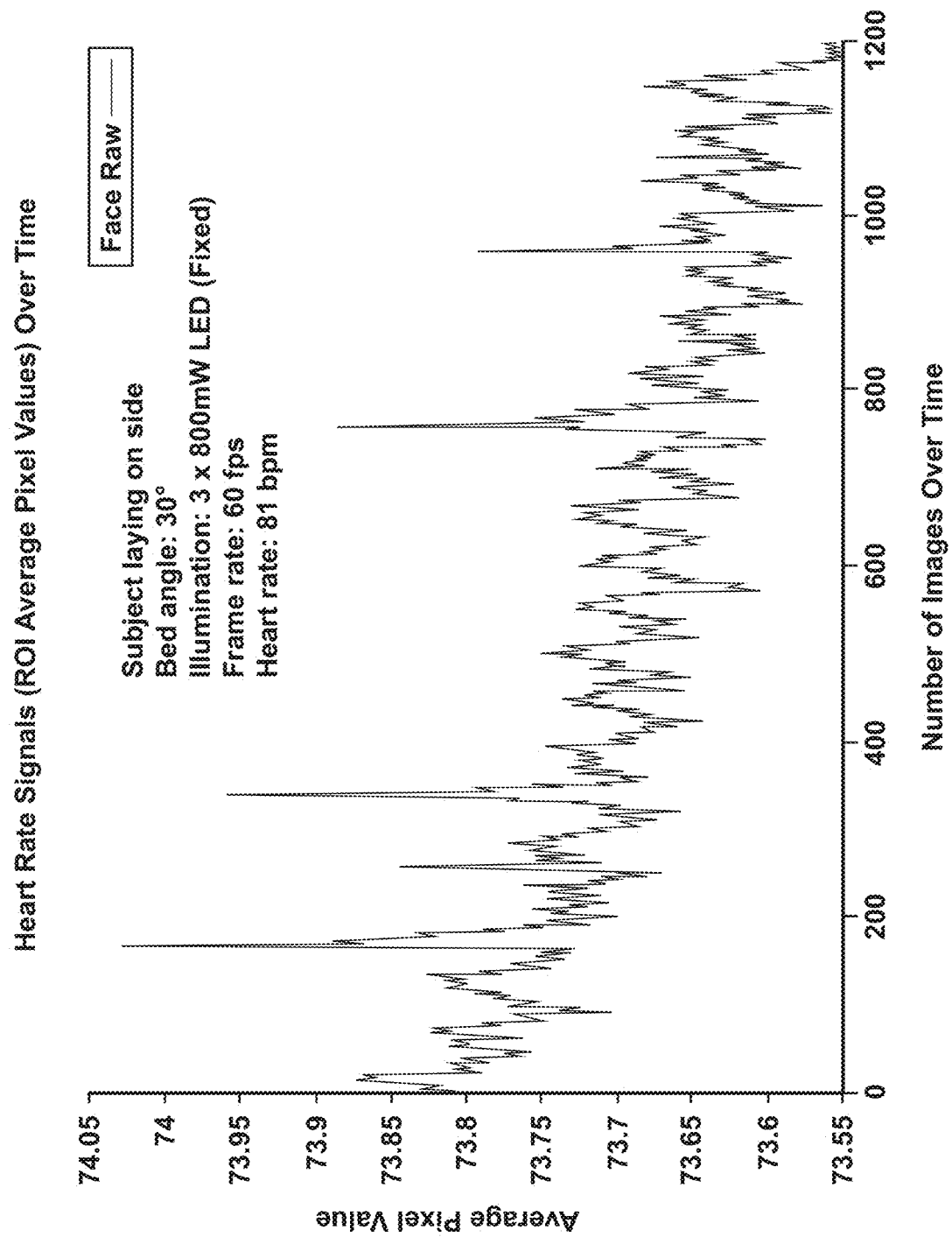
FIG. 13 is a graph of average pixel value compared to the number of images over time to determine a heart rate, according to the present disclosure.

Referring one again to FIG. 8, as well as to FIGS. 12 and 13, the monitoring system 10 is configured to determine the vital signs information 70 of the patient. The vital signs information 70 may include, but is not limited to, a heart rate, a respiration rate, and a facial temperature. The monitoring system 10 may use one or both of the first image data 14 and the second image data 22 for each vital signs determination.

Each of the thermal image frame 190 and the grayscale image frame 210 include the pixels 220, respectively. The controller 30 is configured to analyze the pixels 220 to determine the vital signs information 70. Generally, whether utilizing the thermal image frame 190 or the grayscale image frame 210, the controller 30 calculates or determines a calculated pixel value, which is generally an average pixel value, for a specified area or region in the thermal image frame 190, 210.

For example, the monitoring system 10 is configured to determine the heart rate of the patient. The monitoring system 10 utilizes the facial ROI 34 within the grayscale image frame 210 for this determination. The controller 30 calculates a total number of pixels 220 within the facial ROI 34. The controller 30 also determines a local pixel value for each pixel 220. As previously stated, for grayscale images, each pixel 220 has a single pixel value that corresponds to the brightness of the pixel 220.

The calculated pixel value may be the average pixel value within the facial ROI 34. To calculate the average pixel value, the controller 30 uses the equation:

$$\text{AvePixelVal} = 1/n \cdot \Sigma_{k=1}^{n} P_k,$$

where AvePixelVal or $P_{avg}$ is the average pixel value, $P_k$ is the local or individual pixel value in the specified area (e.g., the facial ROI 34), and n is a total number of pixels 220 in the specified area (e.g., the facial ROI 34). The controller 30 sums the pixel values for each pixel 220 (i.e., from k=1 to k=n) in the facial ROI 34 and divides the summed value by the total number of pixels 220$n$ within the facial ROI 34. It is contemplated that the controller 30 may utilize other practicable calculated pixel values without departing from the teachings herein.

The heart rate of the patient is derived from the pixel variations from the grayscale image frame 210. Pulsatile oxygenated blood flow absorbs NIR light. The absorption of NIR light consequently generates pulsatile pixel variations. These pulsatile pixel variations may be utilized by the controller 30 to determine the heart rate of the patient.

As illustrated in FIGS. 12 and 13, the heart rate is measured when the head of the patient is resting on the head portion 144 of the support apparatus 80 and, consequently, in the head rest zone (i.e., within the operating boundary 192) in the first image data 14. In the illustrated example of FIG. 12, the patient is supine with the head portion 144 of the support apparatus 80 disposed at a 30° angle of elevation. In the example illustrated in FIG. 13, the patient is laying on his or her side with a 30° elevation of the head portion 144. In each of the illustrated examples, the illumination provided for the monitoring system 10 included three 800 mW LEDs and the second imager 20 had a frame rate of 60 frames per second.

The average pixel value is compared to the number of grayscale image frames 210 over time to generate data points, which is the raw data illustrated as solid lines in FIGS. 12 and 13. A predefined number or set of data points are locally detrended. In a specific non-limiting example, such as the example illustrated in FIG. 12, each set of about 200 data points is locally detrended, but any number of data points can be locally detrended without departing from the teachings herein. The local detrend linear function is illustrated in FIG. 12 as the dashed lines $D_1$-$D_6$, each corresponding to a set of 200 data points.

The controller 30 may employ Fast Fourier Transform (FFT) on a predefined number of data points. The predefined number of data points for FFT is greater than the number utilized for the local detrend function. In the illustrated examples, FFT was performed on 1200 data points of locally detrended function to obtain the heart rate. It is contemplated that FFT may be employed on any number of data points without departing from the teachings herein. The heart rate measurement is continuously updated at intervals, for example at every 100 data points. In the illustrated examples, the heart rate measurement was updated every 100 data points, which was approximately every 1.67 seconds. In each of the illustrated examples of FIGS. 12 and 13, the heart rate measurement was 81 beats per minute. As illustrated in FIGS. 12 and 13, the heart rate measurement resolution is about three beats per minute based on the sampling frequency bandwidth of the monitoring system 10. Other resolutions may be utilized without departing from the teachings herein.

The second image data 22 includes multiple grayscale image frames 210 and the heart rate measurement is determined by comparing the pixel values in each frame 210 over time. The controller 30 is configured to determine the average pixel value within the facial ROI 34 in each image frame 210 for the heart rate measurement. The controller 30 is configured to determine the data points, which are generally representative of a relationship between the average pixel value and a number of grayscale image frames 210 over time. The controller 30 is configured to utilize the data points to determine the heart rate of the patient.

Movement of the head position 36 may affect the heart rate measurement of the patient. The movement may cause a new set of data to be obtained for FFT. The movement may be in the x-direction and/or the y-direction. When the movement in one or both directions is greater than a threshold, the monitoring system 10 is triggered to obtain new data points. In this way, each time the movement of the center point 198 and/or the central point 214 exceeds a threshold, the controller 30 is configured to obtain new data and, consequently, obtain a new heart rate measurement. In specific non-limiting examples, when the head position 36 is adjusted greater than or equal to about three inches in the x-direction, the monitoring system 10 is triggered for a new round of acquisition of about 1200 data points. The movement of the head position 36 may be determined in distance (e.g., inches, centimeters, etc.), pixels, coordinate values ($\Delta x$, $\Delta y$), or other practicable methods. The new acquisition provides more accurate image data 14, 22 for the monitoring system 10 to utilize for determining the vital signs information 70.

In another non-limiting example, the controller 30 is configured to determine the respiration rate of the patient using the pixels 220 in at least one of the chest ROIs 216, 218 in multiple grayscale image frames 210 captured as the second image data 22. The controller 30 determines the average pixel value within one or both of the chest ROIs 216, 218. The chest movements from breathing translate into similar pixel variations over a period of time within the fixed chest ROIs 216, 218. The controller 30 monitors the pixel variations over multiple grayscale image frames 210 to determine the pattern in variation, which corresponds with the respiration rate of the patient.

Movement of the patient also affects the determination of the chest ROIs 216, 218 and, consequently, the respiration rate determined by the controller 30. The chest ROIs 216, 218 are configured to be re-mapped and the pixels 220 re-processed based on movement of the head position 36 beyond the threshold. The controller 30 is configured to determine the two chest ROIs 216, 218 utilizing the coordinates of the central point 214 on the grayscale image frame 210. Therefore, when the central point 214 changes in response to movement of the patient, the chest ROIs 216, 218 are also adjusted to realign the chest ROIs 216, 218 relative to the patient to determine the respiration rate.

In an additional non-limiting example, the controller 30 is configured to determine the facial temperature of the patient. The monitoring system 10 generally utilizes the average pixel value from the facial region 32 in the thermal image frame 190 captured as the first image data 14. The pixel values in the thermal image frame 190 may be processed similarly to those of the grayscale image frames 210, where each pixel 220 is assigned a local pixel value that is analyzed by the controller 30. The local pixel values may be used to determine a calculated or average pixel value. The change in temperature may be monitored over multiple thermal image frames 190 based on a change in the local pixel values and the average pixel value.

Figure 14:
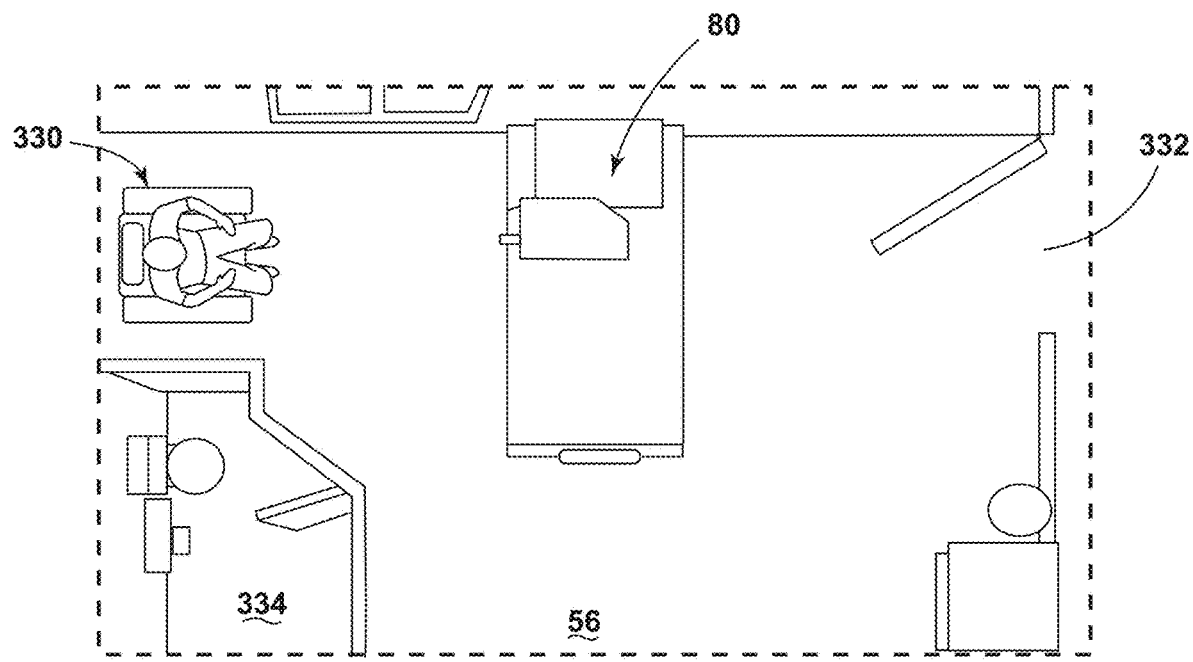
FIG. 14 is a schematic diagram of a patient room in a medical facility, according to the present disclosure.
Figure 15:
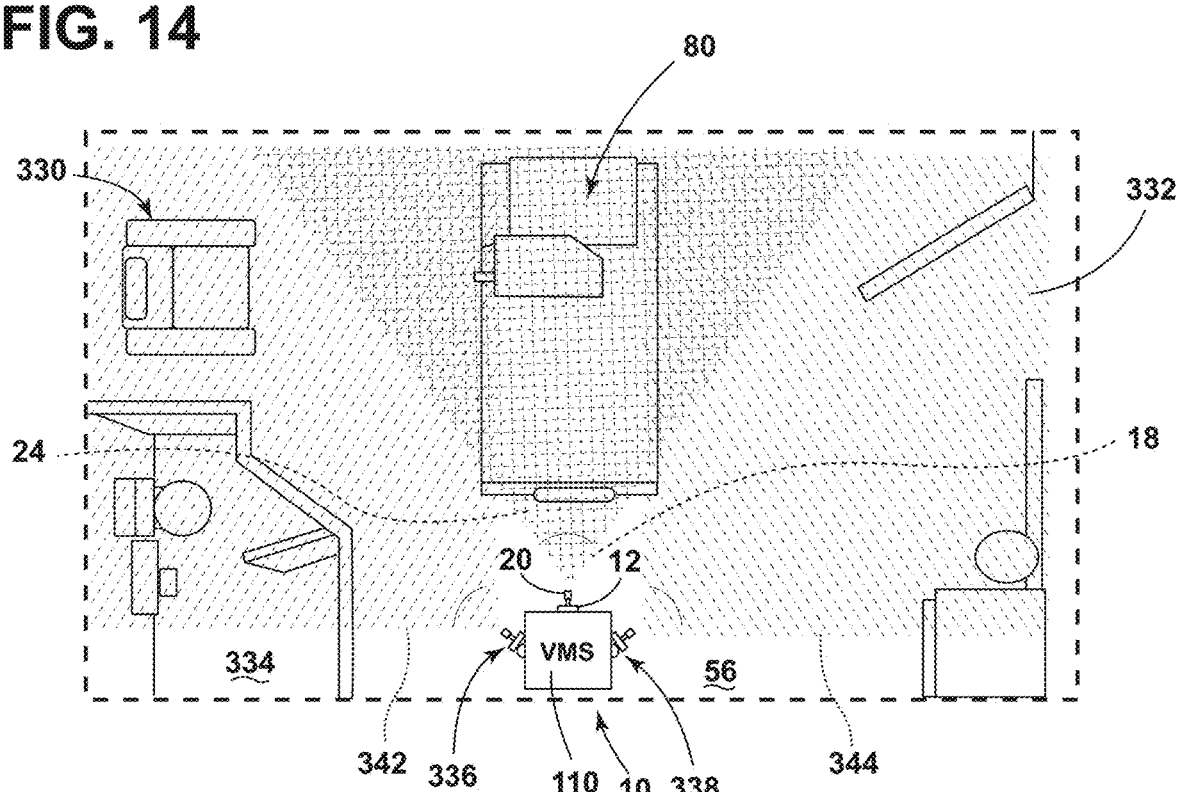
FIG. 15 is a schematic diagram of a patient room with multiple fields of view where image data is captured by a monitoring system, according to the present disclosure.

Referring to FIGS. 14 and 15, the monitoring system 10 may be utilized to track and monitor the vital signs information 70 and patient movement on the support apparatus 80, as well as patient movement outside the support apparatus 80 within the patient room 56. An exemplary patient room 56 is illustrated in FIG. 14, which includes the support apparatus 80 generally configured as a bed, a secondary support apparatus 330 generally configured as a chair, a room exit 332 that allows the patient to exit the patient room 56, and a restroom 334.

The first and second imagers 12, 20 each define the respective fields of view 18, 24, which collectively encompass the support apparatus 80 and an area adjacent to the support apparatus 80. The first and second fields of view 18, 24 are primarily utilized for monitoring the patient movement on the support apparatus 80, as well as for determining the vital signs information 70. The first and second fields of view 18, 24 each have an angle view in a range between about 50° and about 60°. The first and second fields of view 18, 24 extend over and encompass the support apparatus 80. Generally, the operating boundaries 192, 212 outline a periphery of the support apparatus 80. The first and second imagers 12, 20 may be utilized to monitor the position of the patient within the operating boundaries 192, 212 by monitoring changes in the position or coordinate of the center point 198 in the first image data 14 and the central point 214 in the second image data 22. Other areas within the patient room 56 may not typically fall within the first field of view 18 or the second field of view 24.

The monitor assembly 110 may include additional imagers 336, 338 for monitoring the patient movement within the patient room 56 outside of the support apparatus 80. A first side imager assembly 336 and a second side imager assembly 338 may be selectively and removably coupled to opposing sides of the housing 112 of the monitor assembly 110. Generally, the monitor assembly 110 includes connector ports 340, such as universal serial bus (USB) ports, to removably couple the side imager assemblies 336, 338 with the remainder of the monitor assembly 110. Once connected with the connector ports 340, the side imager assemblies 336, 338 are in communication with the controller 30 of the monitoring system 10.

In the illustrated example, the side imager assemblies 336, 338 are positioned on opposing sides of the first and second imagers 12, 20. It is contemplated that both of the side imager assemblies 336, 338 may be positioned on a same side relative to the first and second imagers 12, 20 depending on the configuration of the patient room 56. The configuration of the monitor assembly 110 may be adjusted or varied based on the configuration of the patient room 56 such that the monitor assembly 110 obtains image data of at least a substantial portion of the patient room 56.

The first side imager assembly 336 defines a first side field of view 342, which generally extends over a first portion or a first side of the patient room 56. The first side imager assembly 336 is configured to obtain image data of the first side field of view 342 and communicate the image data to the controller 30. The second side imager assembly 338 defines a second side field of view 344 extending over a second portion or a second side of the patient room 56, which is illustrated on an opposing side of the support apparatus 80 relative to the first side field of view 342. The second side imager assembly 338 is configured to obtain image data of the second side field of view 344 and communicate the image data to the controller 30.

In the illustrated configuration provided in FIGS. 14 and 15, the first and second fields of view 18, 24 extend between and partially overlap each of the side fields of view 342, 344, thereby providing four fields of view 18, 24, 342, 344 in the patient room 56. In the illustrated example, the first side field of view 342 monitors a first area, which encompasses an area proximate to the support apparatus 80, including a first side of the support apparatus 80, the secondary support apparatus 330, and the door to the restroom 334. The second side field of view 344 encompasses a second area proximate to the support apparatus 80, including an opposing side of the support apparatus 80 and the room exit 332. Accordingly, as illustrated in FIG. 15, a substantial portion of the patient room 56 is monitored through the monitoring system 10 having the side imager assemblies 336, 338 as the various fields of view 18, 24, 342, 344 extend over and encompass at least a substantial portion of the patient room 56. In this way, the movement of the patient outside of the support apparatus 80 may be monitored through the contactless monitoring system 10.

Figure 16:
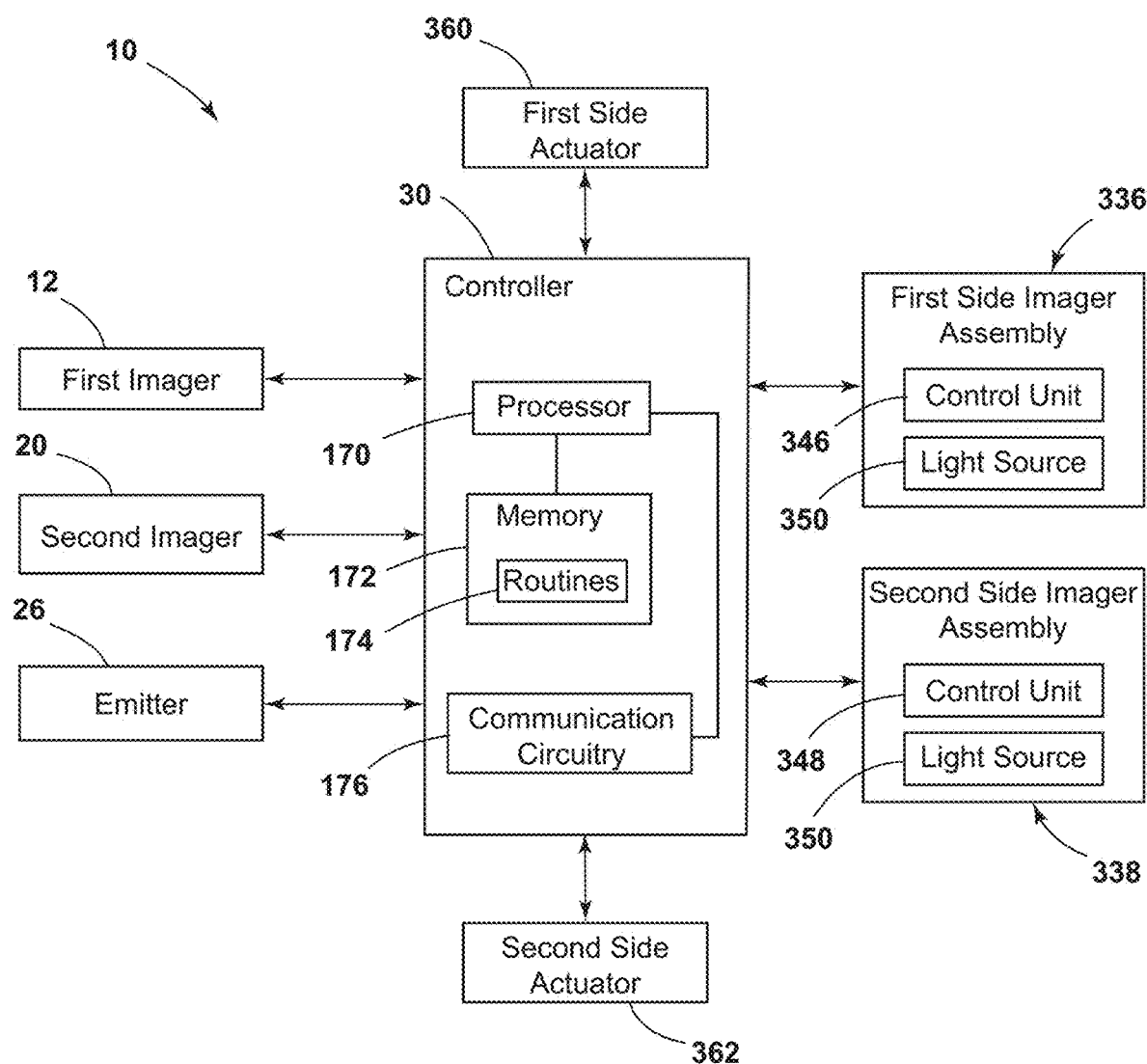
FIG. 16 is a block diagram of a monitoring system with side imager assemblies, according to the present disclosure.

Referring to FIG. 16, each of the side imager assemblies 336, 338 includes a control unit 346, 348, respectively. Each control unit 346, 348 includes a processor, a memory, and other control circuitry. Instructions or routines are stored within the memory and executable by the processor. A lens for each of the side imager assemblies 336, 338 may be selected such that the fields of view 342, 344 generally provide an angle of view between about 80° and about 90°. Each of the first and second side imager assemblies 336, 338 may be high-resolution camera modules to provide higher quality images to the controller 30, without fisheye deformation obtained using wider angled lenses. Each of the side imager assemblies 336, 338 may include a charge coupled device (CCD), a complementary metal oxide semiconductor (CMOS) imager, or any type of monochromatic camera.

The side imager assemblies 336, 338 also include a light source 350. The light sources 350 is generally a NIR LED or an array of NIR LEDs. The NIR LEDs 350 operate to illuminate a respective side or area of the patient room 56. The light may have a wavelength in a range between about 750 nm and about 2,500 nm. In various examples, the light emitted by the light sources 350 may have a wavelength in a range between about 750 nm and about 1,500 nm. It is contemplated that the light sources 350 may continually emit light when the monitoring system 10 is activated and/or when the side imager assemblies 336, 338 are activated, respectively, to provide illumination for the side imager assemblies 336, 338 to continually capture the image data. The side imager assemblies 336, 338 are generally not equipped with or free of an infrared (IR) or NIR filter, which allows monitoring within the patient room 56 during the day and at night (i.e., during different lighting conditions). However, the side imager assemblies 336, 338 may be utilized with an IR filter without departing from the teachings herein.

Figure 17A:
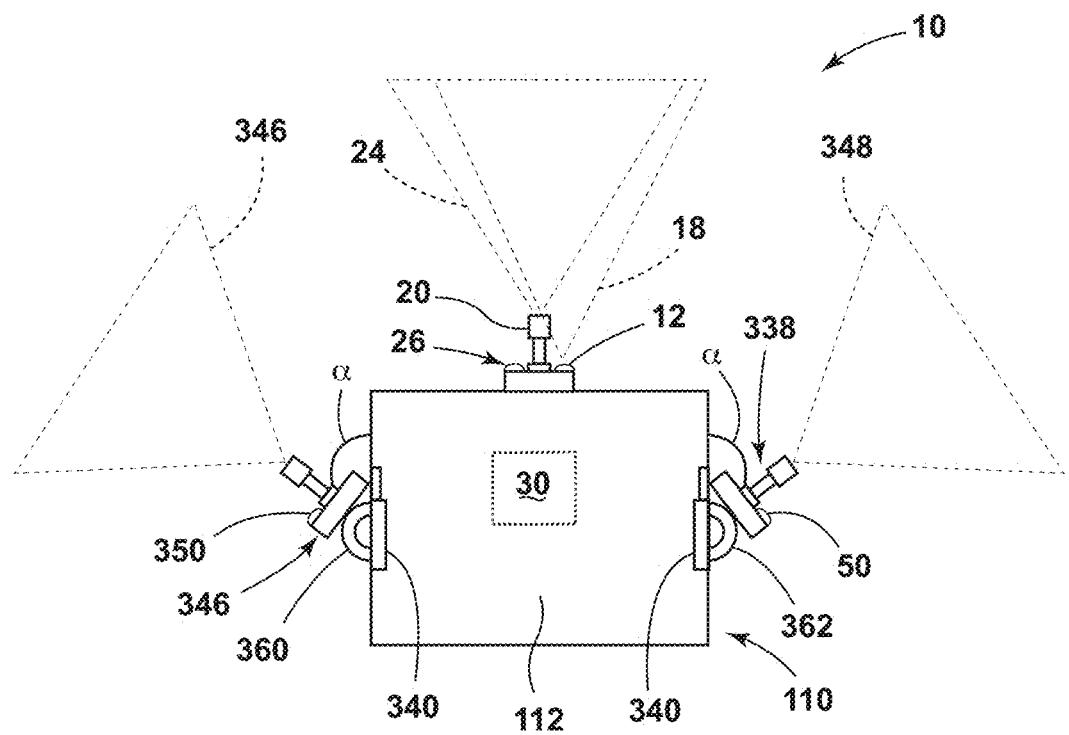
FIG. 17A is a schematic diagram of a monitoring system with side imager assemblies in a first position, according to the present disclosure.
Figure 17B:
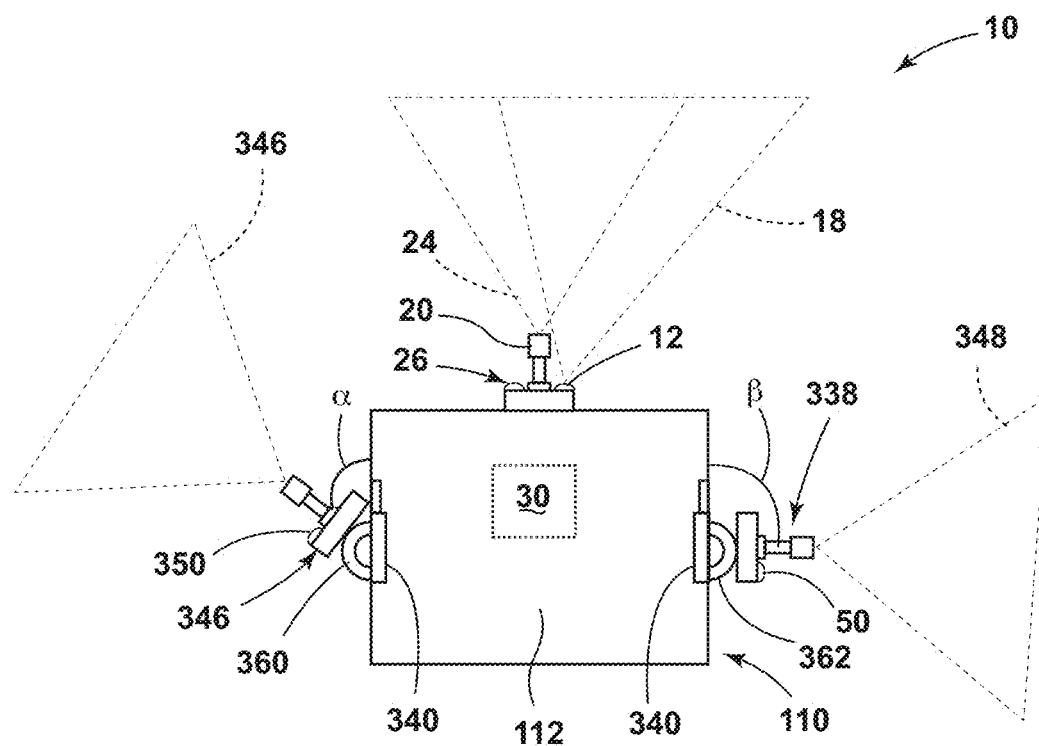
FIG. 17B is a schematic diagram of the monitoring system of FIG. 17A with one side imager assembly in the first position and another side imager assembly in a second position, according to the present disclosure.

Referring still to FIG. 16, as well as FIGS. 17A and 17B, the illustrated monitoring system 10 includes a first side actuator 360 and a second side actuator 362. Additional actuators may be included in the monitor assembly 110 without departing the teachings herein. In a specific non-limiting example, the side actuators 360, 362 are ball joint mechanisms configured to be adjusted by the controller 30. The ball joint side actuators 360, 362 are controlled by the controller 30 to rotate or otherwise be adjusted relative to the housing 112.

Each of the side imager assemblies 336, 338 is coupled to the housing 112 via the side actuators 360, 362, respectively. Coupling the side imager assemblies 336, 338 to the housing 112 via the ball joint side actuators 360, 362 allows the controller 30 to adjust the orientation of the side imager assemblies 336, 338. Adjusting the orientation of the side imager assemblies 336, 338 relative to the housing 112 allows the orientation of the fields of view 342, 344 to be adjusted. The orientation of the side imager assemblies 336, 338 may be adjusted based on detected patient movement, predefined settings, orientation of the patient room 56, an input from the caregiver, or other factors.

As illustrated in FIG. 17A, the first side imager assembly 336 and the second side imager assembly 338 are each oriented at a first angle $\alpha$ relative to the housing 112, extending toward the first and second imagers 12, 20. The first angles $\alpha$ are generally mirror images of one another. As illustrated in FIG. 17B, the second side imager assembly 338 has been rotated to be oriented at a second angle $\beta$ relative to the housing 112, which is a greater angle than the first angle $\alpha$. It is contemplated that the using ball joint side actuators 360, 362, the side imager assemblies 336, 338 may be adjusted vertically, horizontally, at angles, rotated, or adjusted in any direction or manner accommodated by the housing 112. The adjustable side imager assemblies 336, 338 provide the monitoring system 10 with the ability to capture image data from any location, or almost any location, within the patient room 56 to provide increased care to the patient.

Referring again to FIGS. 14-17B, the monitoring system 10 is configured to monitor the movement of the patient and determine when the patient is exiting the support apparatus 80. In such circumstances, the monitoring system may trigger a bed exit or fall risk protocol. When this protocol is activated, the patient may not exit the bed or the chair or other support apparatus 80, 330 without the assistance of a caregiver due to a heightened risk that the patient may fall or be injured. For example, when the fall risk protocol is activated, the controller 30 monitors the movement of the patient for potential egress from the support apparatus 80. The monitoring system 10 may utilize position information 352 from the image data 14, 22 to determine whether the patient movement indicates that the patient intends to exit the support apparatus 80. If the movement of the patient is indicative of an intent to exit the support apparatus 80, the controller 30 may generate an alert for the caregiver that the patient is attempting to exit the bed.

Additionally or alternatively, the monitoring system 10 may determine whether the caregiver is in the patient room 56 as the patient is attempting to exit the support apparatus 80. The monitoring system 10 may identify the caregiver within the fields of view 18, 24, 342, 344 that encompass the patient room 56. The caregiver may wear an indicator, such as an identifier on credentials, that is identified by the monitoring system 10. The monitoring system 10 may also store caregiver profiles within the memory 172, such that the controller 30 may recognize the caregiver in the image data 14, 22 or the image data from the side imager assemblies 336, 338. When the caregiver is determined to be in the patient room 56, the controller 30 may not generate an alert when the fall risk protocol is activated.

When the patient exits the support apparatus 80, the monitoring system 10 is configured to switch to the appropriate side imager assembly 336, 338. The first and second imagers 12, 20 are utilized to monitor an area adjacent to the support apparatus 80, and the controller 30 is configured to utilize the first and second image data 14, 22 to determine on which side of the support apparatus 80 the patient is exiting. The controller 30 may then activate the side imager assembly 336, 338 that has the field of view 342, 344 that extends on the side of the support apparatus 80 that the patient has exited or intends to exit. Accordingly, the controller 30 is configured to activate the first side imager assembly 336 when the patient moves in a first direction toward the first side field of view 342 and activate the second side imager assembly 338 when the patient moves in a second direction toward the second side field of view 344. The automatic activation of the side imager assemblies 336, 338 provide monitoring of the patient outside of the support apparatus 80, significantly augmenting the care of the patient.

With the side imager assemblies 336, 338, the monitoring system 10 is configured to monitor the patient when the patient is outside of the support apparatus 80 to obtain additional information about the patient. In certain aspects, the side imager assemblies 336, 338 are configured to be moved by the controller 30 in response to sensed movement within the image data 14, 22 of the first and second imagers 12, 20 and/or the image data captured by the side imager assemblies 336, 338. In this way, the monitoring system 10 may generally track the patient and monitor the movement of the patient as the patient moves about the patient room 56 to obtain the additional data. The additional information obtained by the monitoring system 10 generally increases the care of the patient. The caregiver may selectively add or remove the side imager assemblies 336, 338 to the monitor assembly 110 to monitor the patient in other locations within the patient room 56 outside of the support apparatus 80. Once the caregiver couples the side imager assemblies 336, 338 through the connector ports 340, the side imager assemblies 336, 338 are integrated into the monitor assembly 110 to assist in obtaining information about the patient.

For example, the monitoring system 10 may monitor when the patient is on the secondary support apparatus 330 and transitioning between the support apparatus 80 and other locations within the patient room 56 (e.g., the secondary support apparatus 330, the room exit 332, the restroom 334). The monitoring system 10 may also monitor patient behavior, such as when the patient is pulling on his or her lines (e.g., intravenous (IV) lines, catheters, etc.). The monitoring system 10 may also obtain mobility measurements (e.g., speed, gait, distance, etc.) from the patient walking around the patient room 56. The monitoring system 10 may also determine the presence of caregivers and visitors within the patient room 56. Additionally, the monitoring system 10 may monitor patient elopement. Additional information may be obtained by the monitoring system 10 without departing from the teachings herein.

Various aspects of the monitoring system 10 may be activated and deactivated upon certain triggers. For example, when the patient exits the support apparatus 80 into the field of view 342 of the first side imager assembly 336, as detected by the first and second imagers 12, 20, the controller 30 may activate the first side imager assembly 336. When the patient returns to the support apparatus 80 and remains at the support apparatus 80 for a predefined period of time, the first side imager assembly 336 may be deactivated. While the patient is away from the support apparatus 80, the first imager 12 and the second imager 20 may be deactivated. Alternatively, the first imager 12 and the second imager 20 may remain activated continuously. The side imager assemblies 336, 338 may also be continuously active or activated at intervals based on time of day, sensed movement, a pattern of movement of the patient, caregiver input, etc. The monitoring system 10 may provide automated switching between the first and second imagers 12, 20 and the side imager assemblies 336, 338 to provide 24/7 remote patient monitoring.

Further, the monitoring system 10 monitors the patient while the patient is on the support apparatus 80 via the image data 14, 22 captured by the first and second imagers 12, 20, as well as elsewhere in the patient room 56 via the image data captured by the side imager assemblies 336, 338. The orientation of the side imager assemblies 336, 338 may also be continually adjusted via the side actuators 360, 362, respectively. The orientation of the side imager assemblies 336, 338 may be adjusted in response to a caregiver input, predefined setting, sensed movement of the patient, a pattern of movement, time of day, etc.

Referring now to FIG. 18, the monitoring system 10 is generally configured to communicate with other systems and devices within the medical facility 50 via the communication network 178. The monitoring system 10 may communicate with a local server 410 of the medical facility 50. In the illustrated configuration, the local server 410 has a control unit 412 having a processor 414, a memory 416, and other control circuitry. Instructions or routines 418 are stored in the memory 416 and executable by the processor 414. The local server 410 generally includes communication circuitry 420 for communicating via the communication network 178. The local server 410 is also in communication with a facility connected device 422 in the medical facility 50, such as a computer or a status board at a nurse call station via Ethernet 424.

The local server 410 includes software (e.g., routines 418) related to an information system 430 of the medical facility 50. In the illustrated example, the information system 430 includes the local server 410, the facility connected device 422, a remote server 432, a remote device 434, the monitoring system 10, and the support apparatus 80. The information system 430 provides a system for caregivers to communicate with one another, as well as access and share information regarding the patient. The remote server 432 generally stores electronic medical records 436 or other health records for each patient of the medical facility 50. Such electronic medical records 436 may also be stored within the local server 410. Additionally or alternatively, the remote device 434 generally includes a display 438 for viewing information. The remote device 434 may be associated with the caregiver and may be, for example, a phone, a tablet, a laptop, a wearable device, or other remote feature used for viewing or otherwise obtaining information.

Referring still to FIG. 18, the monitoring system 10 is also in communication with the support apparatus 80 via the communication network 178. Information from the support apparatus 80 may be utilized by the monitoring system 10 as a factor in determining vital signs information 70 from the patient. The support apparatus 80 generally includes a control unit 446 having a processor 448, a memory 450, and other control circuitry. Instructions or routines 452 are stored in the memory 450 and executable by the processor 448. The support apparatus 80 also includes communication circuitry 454 for communicating via the communication network 178.

The support apparatus 80 includes a sensor assembly 456 for sensing information about the support apparatus 80 and the patient thereon. In the illustrated example, the sensor assembly 456 includes position sensors 458 for sensing the position of the upper frame 84 such as, for example, the elevated head portion 144. The sensor assembly 456 may also sense a position of each siderail 96, which may indicate a potential egress or exit from the support apparatus 80.

Figure 21:
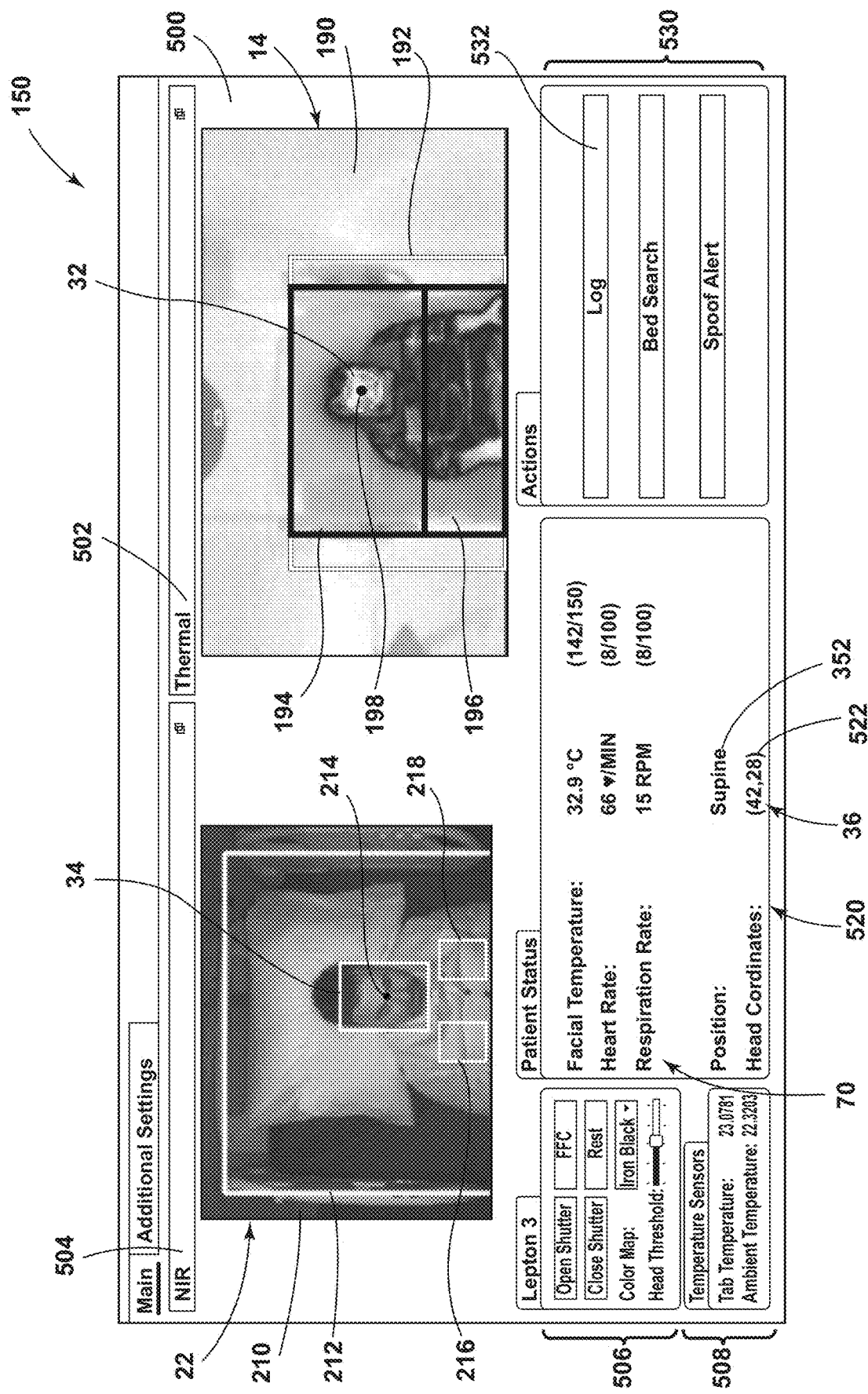
FIG. 21 is illustrative of an application interface displaying image data and patient information obtained from a monitoring system, according to the present disclosure.

The sensor assembly 456 also includes weight sensors 460 for sensing a presence and a position of the patient on the support apparatus 80. The weight sensors 460 may also be utilized as a scale system to monitor a weight of the patient, which may be communicated to the caregiver via the electronic medical record 436 or on the application interface 150 (FIG. 21). The weight sensors 460 may also sense whether an unexpected weight has been added to the support apparatus 80 (e.g., a family member sitting on the support apparatus 80) and provide other data regarding activities surrounding the support apparatus 80.

The sensor assembly 456 may also be associated with a pneumatic system within a mattress or other support feature of the support apparatus 80. The pneumatic system generally includes a plurality of bladders that are independently operable between an inflated condition and a deflated condition via a pump. The sensor assembly 456 may include pressure sensors for sensing a pressure within the bladders and communicating the sensed pressure to the control unit 446. This pressure information may be related to the position or movement of the patient, as well as provide other information about the patient, such as for pressure injury prevention.

The pneumatic system may alter the position of the patient on the support apparatus 80 due to various therapies that may be applied. The condition of the bladders may elevate a portion of the body of the patient or apply different pressures to various areas on the patient. Additionally or alternatively, the bladders may be utilized for rotation therapy, which operates to turn the patient along a longitudinal axis in response to inflation and/or deflation of selected bladders. The bladders may be utilized to provide continuous lateral rotation therapy, which continuously adjusts the patient between a left side and a right side. Moreover, the bladders may be utilized as a part of a turn assist protocol, which assists the caregiver in turning the patient for back care, dressing changes, and other procedures or treatments. Further, the pneumatic system may include fill bladders that operate to fill a space between adjacent segments 86, 88, 90 of the upper frame 84. The information pressure sensors of the sensor assembly 456 may be communicated to the control unit 446 to assist in determining the position of the patient.

Referring still to FIG. 18, the communication network 178 may be part of a network of the medical facility 50. The network may include a combination of wired connections (e.g., Ethernet 424), as well as wireless connections, which may include the wireless communication network 178. The communication network 178 may include a variety of electronic devices, which are configured to communicate over various wired or wireless communication protocols. In the illustrated configuration, the monitoring system 10 is in wireless communication with each of the local server 410, the remote server 432, the remote device 434, and the support apparatus 80. The communication network 178 may include a wireless router through which the remotely accessed devices may be in communication with one another, as well as the local server 410.

The communication network 178 may be implemented via one or more direct or indirect nonhierarchical communication protocols, including but not limited to, Bluetooth®, Bluetooth® low energy (BLE), Thread, Ultra-Wideband, Z-wave, ZigBee, etc. Additionally, the communication network 178 may correspond to a centralized or hierarchal communication network 178 where one or more of the devices communicate via the wireless router (e.g., a communication routing controller). Accordingly, the communication network 178 may be implemented by a variety of communication protocols, including, but not limited to, global system for mobile communication (GSM), general packet radio services, code division multiple access, enhanced data GSM environment, fourth generation (4G) wireless, fifth generation (5G) wireless, Wi-Fi, world interoperability for wired microwave access (WiMAX), local area network, Ethernet 424, etc. By flexibly implementing the communication network 178, the various devices and servers may be in communication with one another directly via the wireless communication network 178 or a cellular data connection.

Each of the controller 30 and the control units 346, 348, 412, 446 disclosed herein may include various types of control circuitry, digital or analog, and may each include a processor 170, 414, 448, a microcontroller, an application specific integrated circuit (ASIC), or other circuitry configured to perform the various inputs or outputs, control, analysis, or other functions described herein. The memories 172, 416, 450 described herein may be implemented in a variety of volatile and nonvolatile memory formats. Routines 174, 418, 452 may include operating instructions to enable the various methods described herein.

Figure 19:
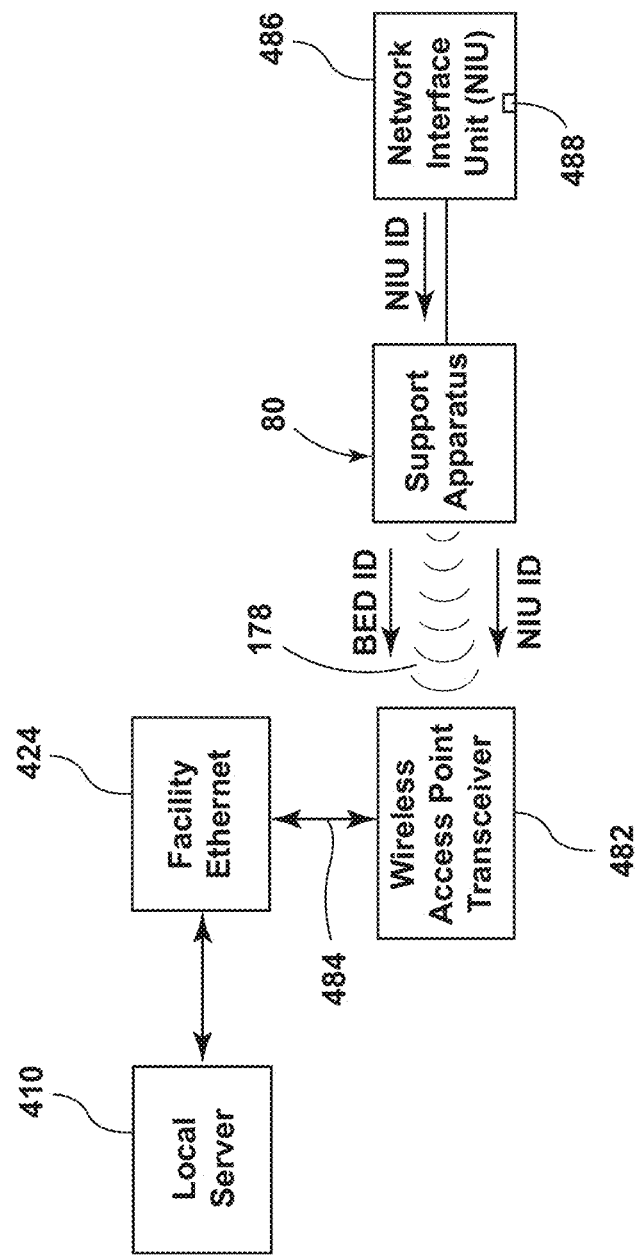
FIG. 19 is a block diagram of a support apparatus wirelessly communicating with a local server via a wireless access point transceiver, according to the present disclosure.
Figure 20:
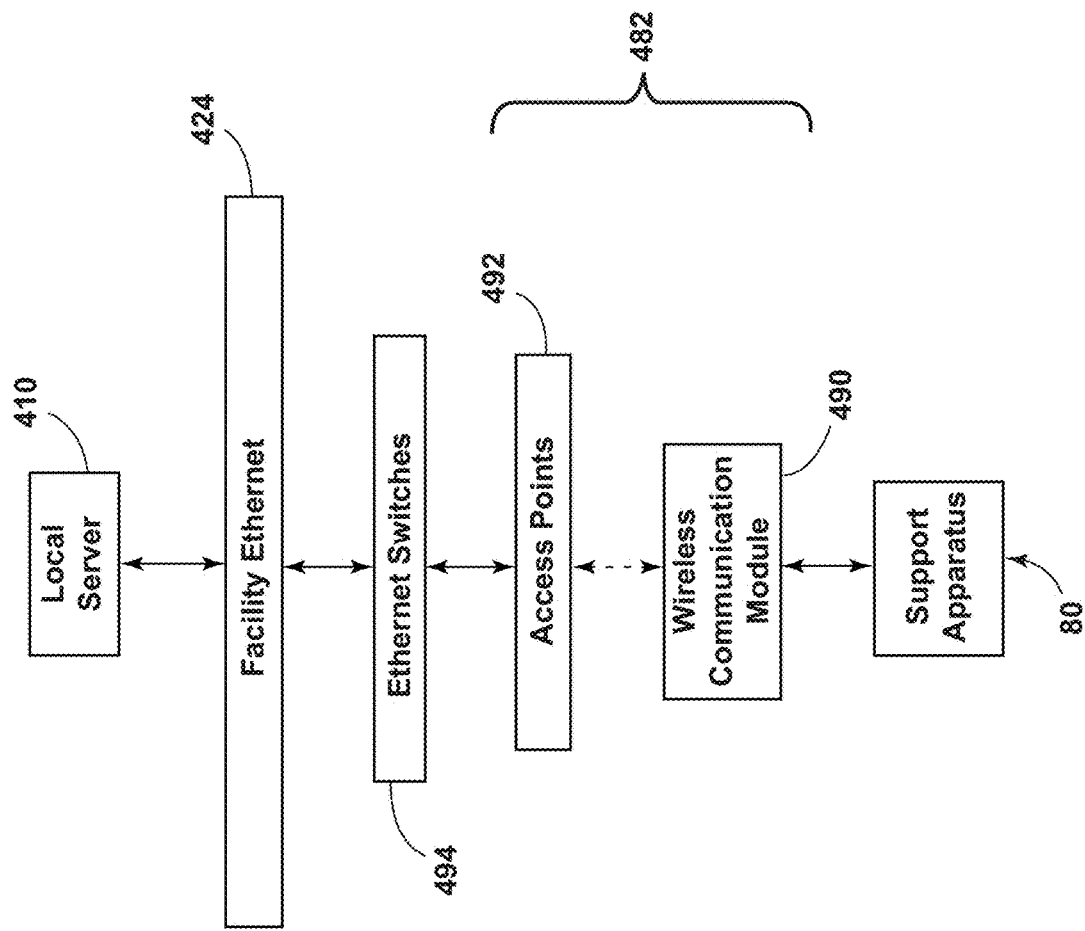
FIG. 20 is a block diagram of a support apparatus wirelessly communicating with a local server via a wireless communication module, according to the present disclosure.

Referring still to FIG. 18, as well as FIGS. 19 and 20, exemplary communications between the support apparatus 80 and the local server 410 are illustrated. The monitoring system 10 may receive information from the support apparatus 80 via the communication network 178 and through the local server 410. In certain aspects, the support apparatus 80 is configured to communicate with a wireless access transceiver 482, which is coupled to Ethernet 424 of the medical facility 50. The communication network 178 provides for bidirectional communication between the support apparatus 80 and the wireless access transceiver 482. The wireless access transceiver 482 communicates bidirectionally with Ethernet 424 via a data link 484.

As illustrated in FIG. 19, the support apparatus 80 may be associated with a network interface unit 486. Multiple network interface units 486 may be provided in various locations within the medical facility 50. Each support apparatus 80 and each network interface unit 486 is assigned a unique identification code, such as a serial number. Various components of the monitoring system 10 and/or the information system 430 on the local server 410 may include software (e.g., routines 418) that operate to associate the identification code of the support apparatus 80 with the network interface unit identification data to locate each support apparatus 80 within the medical facility 50. Each network interface unit 486 includes a port 488 for selectively coupling with Ethernet 424. When the network interface unit 486 is coupled with Ethernet 424, the network interface unit 486 communicates the identification data to the support apparatus 80, which then wirelessly communicates the data for the support apparatus 80 and the network interface unit 486 to the wireless access transceiver 482. The wireless access transceiver 482 then communicates with the local server 410 via Ethernet 424.

As illustrated in FIG. 20, the support apparatus 80 may be capable of communicating wirelessly via a wireless communication module 490. The wireless communication module 490 generally communicates via an SPI link with circuitry of the associated support apparatus 80 (e.g., the communication circuitry 454) and via a wireless 802.11 link with wireless access points 492. The wireless access points 492 are generally coupled to Ethernet switches 494 via 802.3 links. It is contemplated that the wireless communication modules 490 may communicate with the wireless access points 492 via any of the wireless protocols disclosed herein. Additionally or alternatively, the Ethernet switches 494 may generally communicate with Ethernet 424 via an 802.3 link. Ethernet 424 is also in communication with the local server 410, allowing information and data to be communicated between the local server 410 and the support apparatus 80.

Referring again to FIG. 18, as well as to FIG. 21, the monitoring system 10 is in communication with the support apparatus 80 and the remote server 432 to obtain information from the support apparatus 80 and the electronic medical records 436. The monitoring system 10 may compare the currently detected vital signs information 70 with previous vital signs information 70 or may compare the vital signs information 70 with the position of the patient on the support apparatus 80. The monitoring system 10 may compare detected vital signs information 70 with baseline information stored in the electronic medical record 436. Based on the information from the support apparatus 80 and/or the electronic medical record 436, the monitoring system 10 may then trigger an alert to the caregiver based on the detected information. Additionally or alternatively, the monitoring system 10 may combine information from the monitoring system 10, the electronic medical record 436, and/or the support apparatus 80 to be displayed on the application interface 150 for the caregiver.

An exemplary application interface 150 is illustrated in FIG. 21. The application interface 150 includes information from the monitoring system 10 and the support apparatus 80, as well as a way to store the information in the electronic medical record 436. Each of the remote device 434 and the facility connected device 422 may include an application or software utilized for displaying the application interface 150.

In the illustrated example of FIG. 21, the application interface 150 displays a main or home view 500 associated with the monitoring system 10. The home view 500 includes the thermal image frame 190 and the grayscale image frame 210, each processed by the controller 30. The thermal image frame 190 is included under an identifying title 502 (i.e., "Thermal"). Additionally, in the illustrated example, the thermal image frame 190 includes the operating boundary 192, the first ROI 194, the second ROI 196, and the center point 198 of the facial region 32 visible on the thermal image frame 190.

The grayscale image frame 210 is included proximate to the thermal image frame 190 and under an identifying title 504 (i.e., "NIR"). The grayscale image frame 210 includes the operating boundary 212, the central point 214, the facial ROI 34, and the chest ROIs 216, 218 visible on the grayscale image frame 210. The visibility of the operating boundaries 192, 212 and other visual indicators from the controller 30 allows the caregiver to confirm that the monitoring system 10 is processing appropriate regions on the thermal image frame 190 and the grayscale image frame 210 to obtain the vital signs information 70. The caregiver may also compare the thermal image frame 190 to the grayscale image frame 210 to generally confirm the center point 198 being utilized to map the facial ROI 34. Further, the caregiver may confirm the alignment between the monitor assembly 110 and the support apparatus 80 and that the patient is included in the first and second image data 14, 22. The thermal image frame 190 and the grayscale image frame 210 displayed on the application interface 150 may be the most recent image data 14, 22, the image data 14, 22 analyzed to determine the vital signs information 70 displayed on the application interface 150, or any other relevant image data 14, 22.

The application interface 150 also includes setting information 506 related to at least the first imager 12, which is included under an identifying title (i.e., "Lepton 3"). The setting information 506 includes shutter settings for an open shutter and a closed shutter of the first imager 12. The open shutter settings include flat field correction, which may be utilized to calibrate an image sensor or image sensors within the first imager 12. Other setting information 506 includes a type of color map that is utilized for the first image data 14 and a head threshold. Each of the settings may be adjusted by the caregiver via the application interface 150. Additional settings may be accessed and adjusted on a secondary view on the application interface 150 (e.g., "Additional Settings").

Additionally, the application interface 150 displays temperature information 508 from the monitoring system 10, including the ambient temperature and the reference tab temperature. The ambient temperature and the reference tab temperature are utilized for calibrating and/or correcting temperature sensed by the first imager 12. Further, the reference tab 132 may be utilized to increase the temperature measurement accuracy of the first imager 12. The caregiver may also monitor the ambient temperature to increase comfort and improve care for the patient within the patient room 56.

Referring still to FIG. 21, the application interface 150 displays patient information 520 from the monitoring system 10 and the support apparatus 80. The patient information 520 generally includes the vital signs information 70 determined by the monitoring system 10, including, for example, the facial temperature, the heart rate, and the respiration rate of the patient. The vital signs information 70 may be obtained from the thermal image frame 190 and/or the grayscale image frame 210 displayed on the application interface 150. Additionally or alternatively, the vital signs information 70 may be obtained from multiple image frames 190, 210 that collectively form the first and second image data 14, 22. In such examples, additional thermal and grayscale image frames 190, 210 may be viewed on the application interface 150.

The patient information 520 also includes head coordinates 522 that correspond to the center point 198 in the thermal image frame 190 and the central point 214 in the grayscale image frame 210 (i.e., the head position 36). The head coordinates 522 are monitored by the monitoring system 10 to detect the movement of the patient, as described herein. The monitoring system 10 may initiate additional acquisition of the image data 14, 22 and again determine vital signs information 70 from the patient in response to a change in the head coordinates 522.

Additionally, the patient information 520 includes the position information 352 related to the position of the patient on the support apparatus 80. As previously stated, the monitoring system 10 monitors and determines the position of the patient, for example, supine, sitting, out of bed, etc. The monitoring system 10 is configured to track the center point 198 of the thermal image frame 190 and determine patient movement in response to the position (i.e., the coordinates) of the center point 198. It is contemplated that the position information 352 may also include the position of the support apparatus 80, for example, the elevated head portion 144, an elevated foot portion, etc. The position of the support apparatus 80 may be utilized for tracking the patient movement for determining the vital signs information 70.

Referring still to FIG. 21, the application interface 150 also includes an interactive actions section 530 that the caregiver may utilize to take certain steps in response to the information displayed on the application interface 150. For example, a log 532 feature may allow the caregiver to store the information from and/or an image of the application interface 150 into the electronic medical records 436 stored within the remote server 432. Other actions may be customizable or personalized based on the medical facility 50, the monitoring system 10, or other factors.

Referring to FIGS. 22-31, the remote device 434 may include an application or software for displaying the application interface 150 and providing communication between multiple remote devices 434. The information system 430 allows different caregivers associated with the patient to convey or share information that may not be more formally stored within the electronic medical records 436. A communication aspect of the information system 430 generally provides more convenient and efficient communication between the caregivers associated with the patient.

Figures 22, 23:
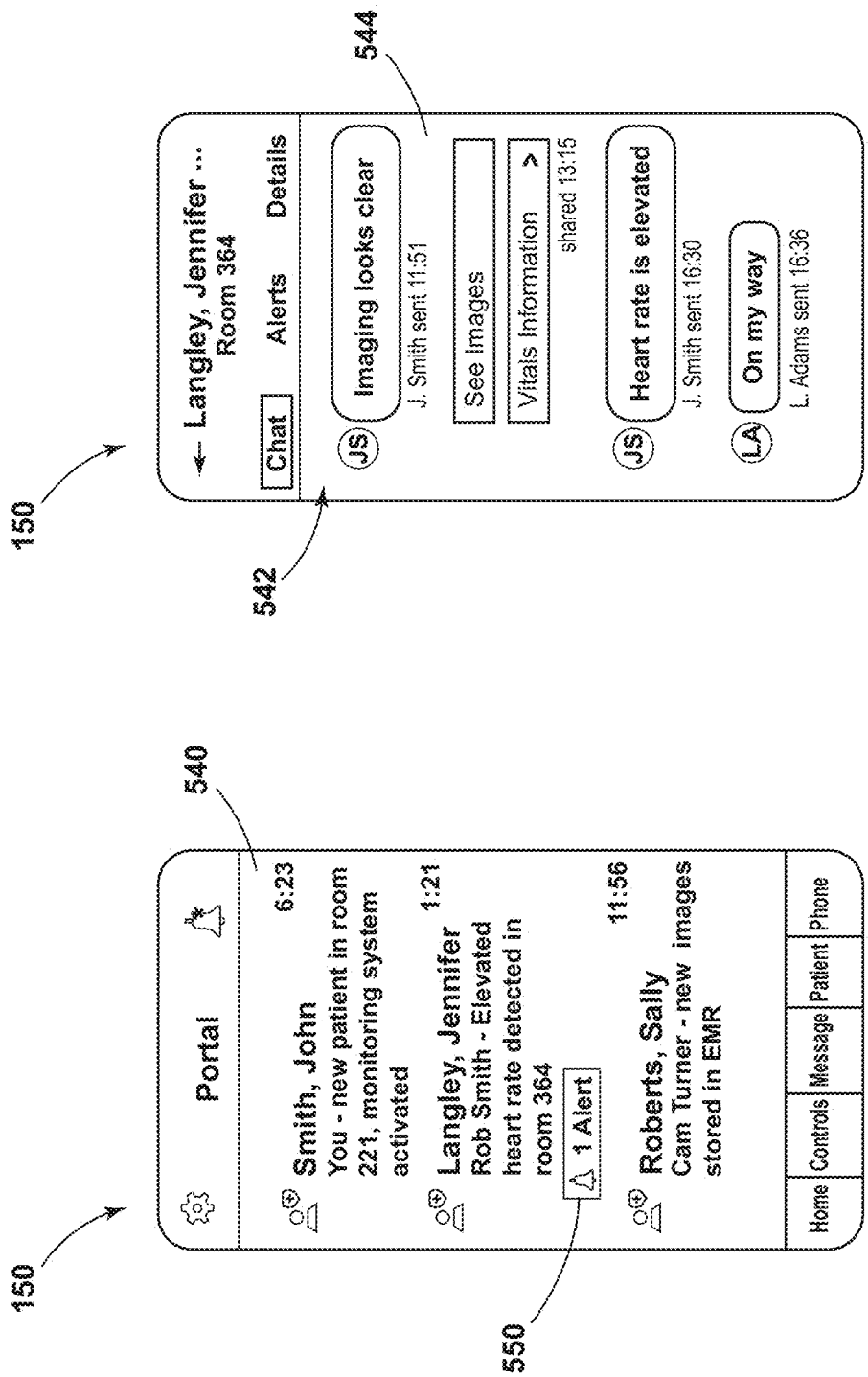
FIG. 22 is illustrative of an application interface displaying a communication portal, according to the present disclosure.
FIG. 23 is illustrative of an application interface displaying a chat feature in a patient profile, according to the present disclosure.

As illustrated in FIG. 22, the application interface 150 is configured to display a communication portal 540 for each caregiver, which includes multiple patient profiles 542 that can be accessed through the communication portal 540. Each patient profile 542 corresponds to one patient associated with the caregiver. Each caregiver associated with the patient is granted access to the respective patient profiles 542. Additionally or alternatively, the communication portal 540 provides a way for each caregiver associated with the patient to communicate with one another, as well as a way to receive and communicate updates about the patient.

Referring to FIG. 23, an exemplary patient profile 542 is illustrated on the application interface 150. The patient profile 542 allows for messaging and sharing information (e.g., a chat feature 544) related to the patient between various caregivers throughout the treatment process of the patient at the medical facility 50. The caregivers may directly message one another through the patient profile 542 while the patient is at the medical facility 50. This communication may be stored within the remote device 434 and may be stored within the electronic medical record 436. Alternatively, the communication portal 540 may provide for sharing information that may not be stored in the electronic medical record 436 of the patient. The chat feature 544 may also provide a way for sharing the information from the monitoring system 10 between different caregivers.

Figures 24, 25:
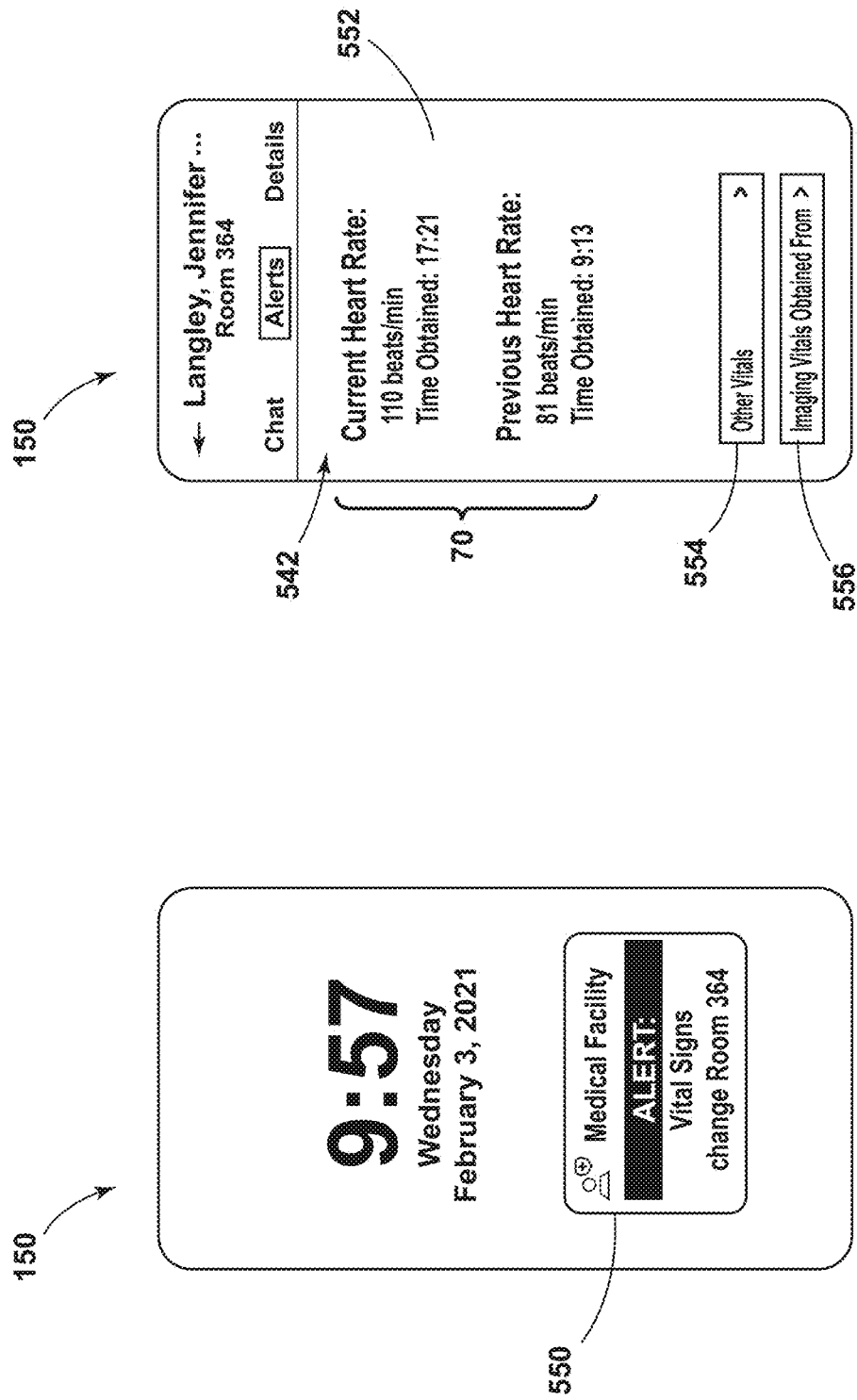
FIG. 24 is illustrative of an application interface displaying an alert notification relating to vital signs information, according to the present disclosure.
FIG. 25 is illustrative of an application interface displaying an alert view relating to vital signs information, according to the present disclosure.

Referring again to FIG. 22, as well as to FIGS. 24 and 25, the controller 30 of the monitoring system 10 may generate an alert feature 550, which is configured to be viewed through the communication portal 540, as illustrated in FIG. 22, or as a push notification, as illustrated in FIG. 24. The monitoring system 10 may provide the visual alert feature 550 on the application interface 150 through the communication portal 540, the patient profile 542, a locked screen of the remote device 434, etc. The push notification may be advantageous for alerting the caregiver when the application interface 150 is not actively being displayed on the communication portal 540. Additionally or alternatively, the monitoring system 10 may provide an audible or tactile alert feature 550 on the remote device 434 or the facility connected device 422, such as through the nurse call station.

The caregiver may select the visual alert feature 550 on the communication portal 540, causing the application interface 150 to subsequently display an alert view 552 in the patient profile 542, as illustrated in FIG. 25. In the illustrated example, the application interface 150 displays a current detected heart rate determined by the monitoring system 10 and a previous heart rate. The previous heart rate may have been previously obtained from the monitoring system 10 or may have been retrieved in the electronic medical record 436, including a baseline measurement or any previous measurement.

The monitoring system 10 may compare the currently detected vital signs information 70 with previously detected vital signs information 70 and/or previously stored vital signs information 70 to generate the alert feature 550. The alert feature 550 may be generated when the vital signs information 70 exceeds a threshold or a threshold range, falls below a threshold or a threshold range, or when a change in the vital signs information 70 exceeds a threshold or a threshold range. When the application interface 150 is displaying the alert view 552, the application interface 150 may also display selectable features 554, 556 to display other vital signs information 70 and the imaging from which the vital signs information 70 was obtained, respectively.

Figure 26:
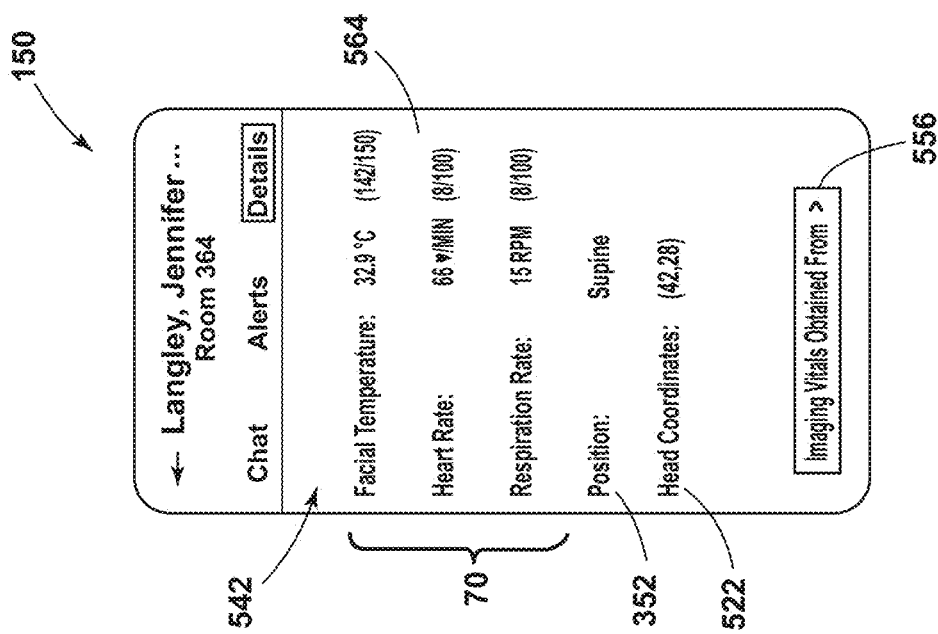
FIG. 26 is illustrative of an application interface displaying patient information, according to the present disclosure.

Referring to FIG. 26, the application interface 150 may include a detail view 564 related to the patient. On the detail view 564, the application interface 150 generally displays the patient information 520, including the vital signs information 70, the position of the patient on the support apparatus 80, and the head coordinates 522. The detail view 564 may be customizable for the patient to allow the caregiver to view current information relevant to treatment or care in a single location.

Figure 27:
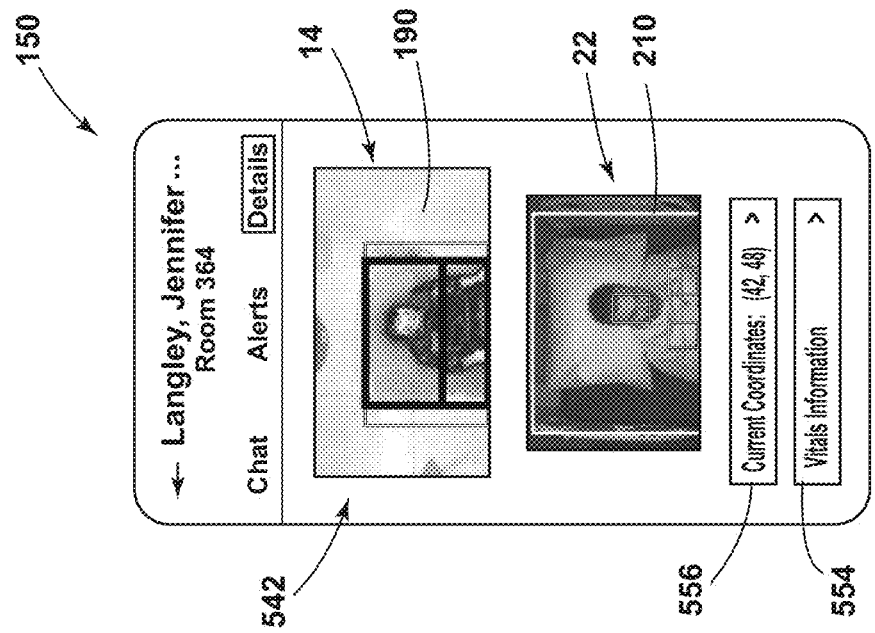
FIG. 27 is illustrative of an application interface displaying image data obtained by a monitoring system, according to the present disclosure.

Referring to FIG. 27, the application interface 150 displays the first and second image data 14, 22 for viewing by the caregiver. The caregiver may then view the quality of the image, as well as verify the facial region 32 in the first image data 14 and the ROIs 34, 216, 218 within the second image data 22 that are utilized to determine the vital signs information 70. The caregiver may also compare the displayed imaging to the current head coordinates 522 displayed on the application interface 150. Viewing the first and second image data 14, 22 may be advantageous for the caregiver to confirm or verify the functions of the monitoring system 10.

Figure 29:
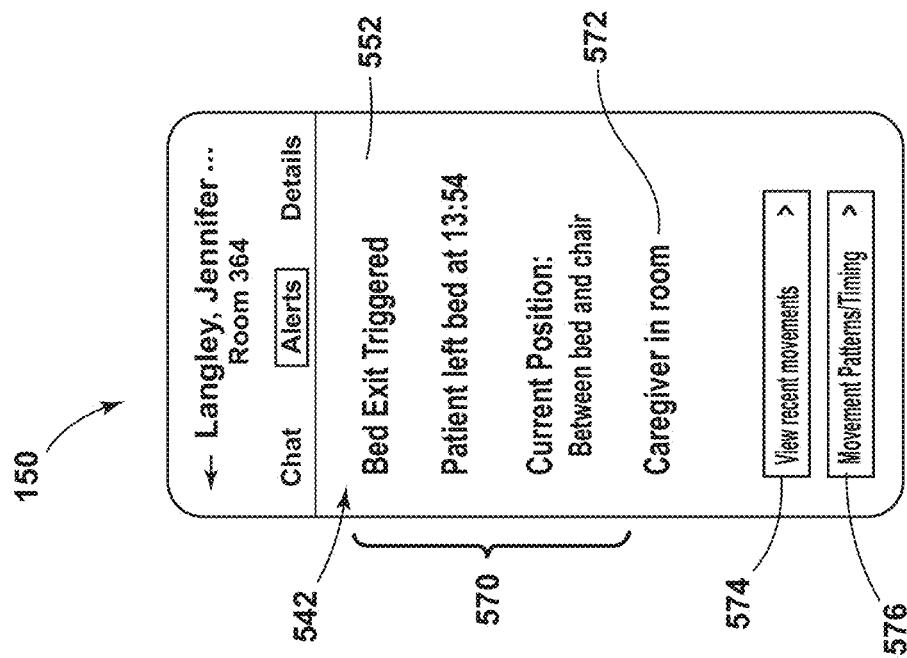
FIG. 29 is illustrative of an application interface displaying an alert view relating to patient movement, according to the present disclosure.
Figure 28:
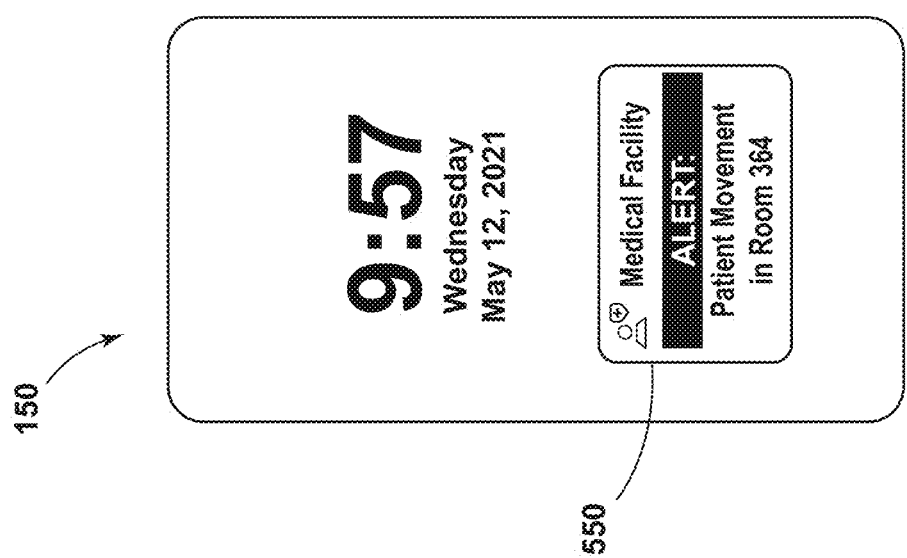
FIG. 28 is illustrative of an application interface displaying an alert notification relating to patient movement, according to the present disclosure.

Referring to FIGS. 28 and 29, the alert feature 550 may be generated in response to the movement of the patient, such as egress from the support apparatus 80, falling, pulling on lines, etc. As illustrated in FIG. 29, the application interface 150 may include movement information 570 in the alert view 552. The movement information 570 may include, for example, that the bed exit protocol has been triggered by egress from the support apparatus 80. The movement information 570 may also include a location of the patient within the patient room 56, movement patterns, mobility measurements, or any practicable movement information 570 that may assist in caring for the patient.

Additionally or alternatively, the controller 30 may determine the timing of the movement of the patient, including, for example, a time when the patient exited the bed, a time the patient is out of the bed, a return time to the bed, etc. The application interface 150 may also include information relating to a current position of the patient or others in the patient room 56 based on the image data 14, 22 from the first and second imagers 12, 20, as well as the image data obtained by the side imager assemblies 336, 338. Further, the monitoring system 10 may detect personnel information 572, which generally indicates whether the caregiver is in the patient room 56 or if the additional person in the patient room 56 is a visitor. The personnel information 572 may also include information about the caregiver timing information (e.g., time the caregiver is in the patient room 56, last caregiver visit, etc.). The alert view 552 may also include a selectable feature 574 for viewing recent movements of the patient and a selectable feature 576 for viewing movement patterns and timing. Additional selectable features may be included without departing from the teachings herein.

Figure 31:
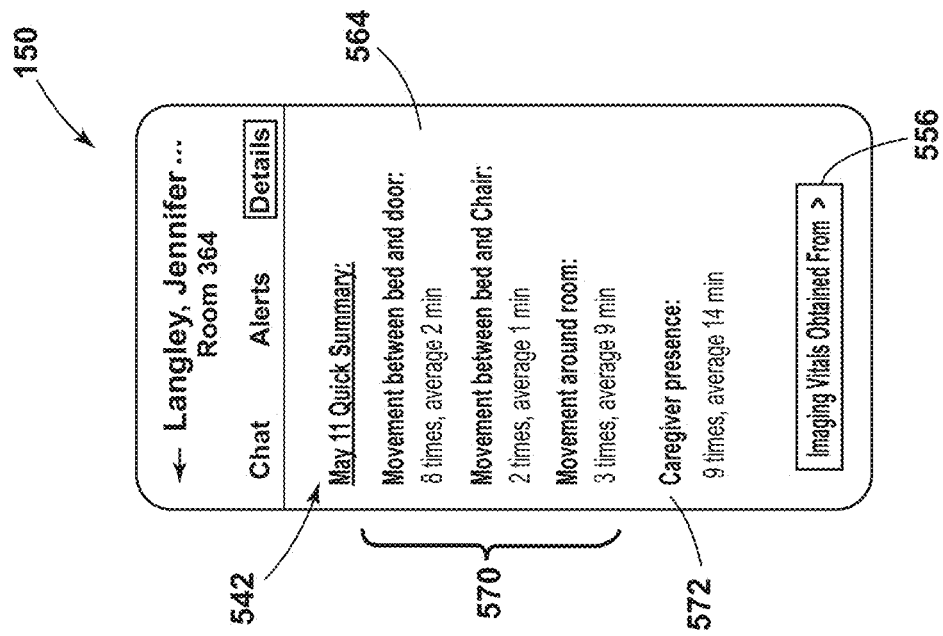
FIG. 31 is illustrative of an application interface displaying a detail view relating to patterns of patient movement, according to the present disclosure.
Figure 30:
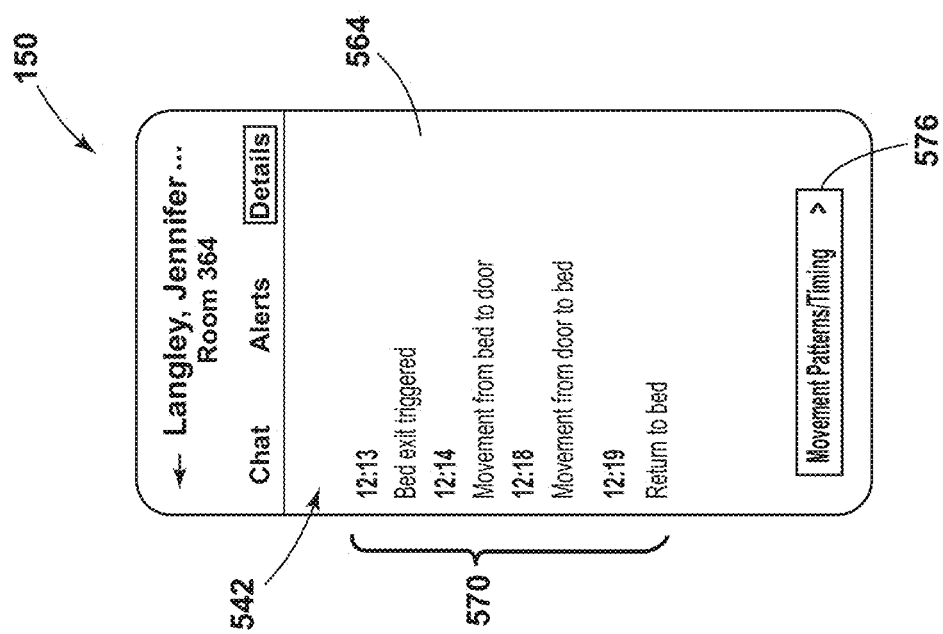
FIG. 30 is illustrative of an application interface displaying a detail view relating to patient movement, according to the present disclosure.

With reference to FIGS. 30 and 31, the detail view 564 of the application interface 150 may include additional movement information 570. For example, as illustrated in FIG. 30, the monitoring system 10 may detail a time and a type of detected movement of the patient. The application interface 150 may display the time when a specific movement is detected and display a list of the recent movements of the patient. The caregiver may utilize this movement information 570 to monitor the mobility of the patient. As illustrated in FIG. 31, the controller 30 may analyze the movement of the patient to provide patterns and timing for the caregiver. The controller 30 may summarize repeated movement and average times for the specific movements. The patterns may indicate mobility of the patient, caregiver patterns, etc. Additional or alternative movement information 570 may be determined by the controller 30 and communicated to the caregiver without departing from the teachings herein.

Referring to FIGS. 21-31, the communication aspect of the information system 430 provides a convenient and efficient way for the caregiver to view the information obtained by the monitoring system 10. Depending on the configuration of the application interface 150, the caregiver may view the information simultaneously or on subsequently displayed images. The caregiver may also activate and deactivate the monitoring system 10 from the application interface 150. Moreover, the caregiver may be alerted by the monitoring system 10. Further, the caregivers may convey information from the monitoring system 10 between different caregivers through the information system 430. The monitoring system 10, in conjunction with the information system 430, provides a method for contactless monitoring of the patient and subsequent communication between the caregivers to monitor the information obtained by the monitoring system 10.

Referring to FIGS. 1-31, the monitoring system 10 provides a contactless method for monitoring health information of the patient associated with the monitoring system 10. The monitoring system 10 may be activated through the application interface 150 via the remote device 434 or the facility connected device 422 or through a power feature on the monitor assembly 110. Upon activation, the monitoring system 10 may obtain baseline vital signs information 70 and initial position information 352. Alternatively, the baseline vital signs information 70 and/or the initial position information 352 may be obtained by the caregiver using other practicable methods. Once activated, the monitoring system 10 continuously monitors the patient until deactivated by the caregiver.

The monitoring system 10 may be utilized to monitor the movement of the patient. Each instance of the head coordinates 522 being adjusted by the predefined threshold (e.g., pixels, distance, etc.) may be recorded in the electronic medical record 436 and/or communicated to the caregiver via the patient profile 542. The change in head coordinates 522 may trigger a new acquisition of the image data 14, 22 for obtaining the vital signs information 70, the position information 352, or a combination thereof. Further, the monitoring system 10 may determine that the patient is not disposed on the support apparatus 80. If the monitoring system 10 is activated and the patient is not on the support apparatus 80, the monitoring system 10 may activate and/or utilize image data obtained from at least one of the side imager assemblies 336, 338 to monitor the movement of the patient about the patient room 56. The side imager assemblies 336, 338 may also be utilized to monitor different people (e.g., the caregiver, visitors, etc.) within the patient room 56. The monitoring system 10 may also issue an alert to the caregiver that the patient has left the support apparatus 80, left the patient room 56, etc.

Further, the monitoring system 10 is utilized for monitoring the vital signs information 70 of the patient. The monitoring system 10 captures the first image data 14 and the second image data 22, which are each communicated to the controller 30. The first image data 14 is utilized to determine the facial region 32 and the center point 198 of the facial region 32. The center point 198 is mapped onto the second image data 22, such that each of the center point 198 and the central point 214 has the same coordinate within the operating boundary 192, 212 on the first and second image data 14, 22, respectively. Utilizing the center point 198 on the first and the second image data 22, the facial ROI 34 is determined by the controller 30. The chest ROIs 216, 218 are also determined utilizing the facial ROI 34 and the central point 214. The facial and chest regions of interest 34, 216, 218 are utilized to determine vital signs information 70 of the patient being monitored, including, but not limited to, heart rate and respiration rate.

Use of the present system may provide for a variety of advantages. For example, the monitoring system 10 may utilize the first imager 12 to obtain thermal image data 14 and the second imager 20 to obtain monochromatic or grayscale image data 22. Additionally, the monitoring system 10 may utilize the first image data 14 to determine the facial ROI 34 on the second image data 22. Further, the monitoring system 10 may utilize at least one of the first image data 14 and the second image data 22 to obtain the vital signs information 70 of the patient in a contactless manner. Also, the monitoring system 10 may be utilized to track the movement of the patient on the support apparatus 80, as well as out of the support apparatus 80 and elsewhere in the patient room 56. Moreover, the side imager assemblies 336, 338 may be selectively added and removed from the monitor assembly 110 to monitor additional areas within the patient room 56 outside of the support apparatus 80. The monitor assembly 110 with the side imager assemblies 336, 338 may also provide automated patient tracking and trigger alerts.

Further, the monitoring system 10 may be in communication with the remote server 432 and the support apparatus 80 to obtain additional information about the patient that may affect the vital signs information 70. Moreover, the monitoring system 10 may communicate with the remote server 432 and the support apparatus 80 and subsequently generate the alert feature 550 communicated via the application interface 150. Additionally, the monitoring system 10 may be associated with the information system 430 of the medical facility 50. Also, the information system 430 provides the application interface 150 that may be displayed via the remote device 434 and/or the facility connected device 422 to display the vital signs information 70, the patient information 520, the alert feature 550, and other information to the caregiver. Moreover, the information from the monitoring system 10 may be stored within the electronic medical record 436 for the respective patient and may be communicated between caregivers via the communication portal 540. Additional benefits and advantages may be realized and/or achieved.

It is understood that the steps of the method 230 and routines 174 disclosed herein may be performed in any order, simultaneously, repeated, and/or omitted without departing from the teachings provided herein.

The device disclosed herein is further summarized in the following paragraphs and is further characterized by combinations of any and all of the various aspects described therein.

According to one aspect of the present disclosure, a contactless patient monitoring system includes a first imager configured to capture first image data of a target area within a first field of view. A second imager is operably coupled to the first imager. The second imager is configured to capture second image data of the target area within a second field of view. An emitter is operably coupled to at least one of the first imager and the second imager. The emitter is configured to emit light within a predetermined wavelength range. A controller is communicatively coupled to the first imager, the second imager, and the emitter. The controller is configured to determine a facial region of a person in the first image data, determine a region of interest in the second image data that coincides with the facial region in the first image data, and determine at least one coordinate of a head position within the facial region.

According to another aspect of the disclosure, a controller defines a head rest region within first image data.

According to another aspect of the disclosure, at least one coordinate includes an x-coordinate and a y-coordinate of a head position.

According to another aspect of the disclosure, a controller is configured to define an origin position for the x-coordinate and the y-coordinate based on a head rest region.

According to another aspect of the disclosure, at least one coordinate includes an x-coordinate and a y-coordinate of a head position based on an origin position within an operating boundary of first image data.

According to another aspect of the disclosure, a controller is configured to determine whether a predefined period of time has elapsed since determining at least one of an x-coordinate and a y-coordinate.

According to another aspect of the disclosure, a controller is configured to utilize at least one of first image data and second image data to determine vital signs information if a current elapsed time is less than a predefined period of time.

According to another aspect of the disclosure, a controller is configured to determine whether a predefined period of time has elapsed since determining at least one coordinate and utilize at least one of first image data and second image data to determine vital signs information if a current elapsed time is less than the predefined period of time.

According to another aspect of the disclosure, a controller is configured to determine a rate of change in at least one coordinate over a predefined period of time if a predefined period of time has elapsed.

According to another aspect of the disclosure, a controller is configured to determine a rate of change in an x-coordinate over a predefined period of time if the predefined period of time has elapsed.

According to another aspect of the disclosure, a controller is configured to determine a rate of change in a y-coordinate during a predefined period of time if the predefined period of time has elapsed.

According to another aspect of the disclosure, a controller is configured to determine whether at least one of a rate of change in an x-coordinate and a rate of change in a y-coordinate exceeds a predefined threshold.

According to another aspect of the disclosure, a controller is configured to determine vital signs information if each of a rate of change in an x-coordinate and a rate of change in a y-coordinate is less than a predefined threshold.

According to another aspect of the disclosure, a controller is configured to receive a subsequent second image frame if at least one of a rate of change in an x-coordinate and a rate of change in a y-coordinate exceeds a predefined threshold.

According to another aspect of the disclosure, a controller is configured to determine a calculated pixel value within a region of interest in second image data.

According to another aspect of the disclosure, a controller is configured to determine a central point in a region of interest in second image data that corresponds to at least one coordinate in a facial region and determine a chest region of interest in second image data based on the central point.

According to another aspect of the disclosure, a controller is configured to determine at least one of a heart rate and a respiration rate using a calculated pixel value.

According to another aspect of the disclosure, second image data includes multiple image frames. A heart rate is determined by comparing a calculated pixel value in each of the image frames.

According to another aspect of the disclosure, a respiration rate is determined using variations in pixel values within a chest region of interest within second image data over a predefined period of time.

According to another aspect of the disclosure, a first imager, a second imager, and an emitter are coupled to a housing. A side imager assembly is selectively coupled to the housing via an actuator. The side imager assembly is configured to obtain image data within a side field of view that extends adjacent to at least one of a first field of view and a second field of view. A controller is configured to activate the side imager assembly in response to movement of a person within at least one of the first field of view and the second field of view toward the side field of view.

According to another aspect of the disclosure, first and second side imager assemblies are operably coupled to a controller. The first side imager assembly defines a first side field of view that at least partially overlaps with a first field of view of a first imager and the second side imager assembly defines a second side field of view that at least partially overlaps with a second field of view of a second imager. The controller is configured to switch monitoring between the first side imager assembly, the second side imager assembly, and the first and second imagers in response to movement within first image data, second image data, and image data captured by the first and second side imager assemblies.

According to another aspect of the present disclosure, a contactless monitoring system includes a first imager configured to capture first image data of a target area within a first field of view. A second imager is operably coupled to the first imager. The second imager is configured to capture second image data of the target area within a second field of view. A controller is communicatively coupled to the first imager and the second imager. The controller is configured to determine a first selected point in the first image data and determine a second selected point in the second image data that coincides with the first selected point in the first image data.

According to another aspect of the disclosure, a controller is configured to determine a facial region in first image data. A first selected point is a center point within the facial region.

According to another aspect of the disclosure, a controller is configured to determine a facial temperature by calculating an average pixel value within a facial region of first image data.

According to another aspect of the disclosure, a controller is configured to define a head rest region within first image data.

According to another aspect of the disclosure, a controller is configured to determine a region of interest in second image data.

According to another aspect of the disclosure, a controller is configured to determine a heart rate using a region of interest when a head of a patient is positioned in a head rest region.

According to another aspect of the disclosure, a controller is configured to determine an average pixel value in a region of interest. The controller is configured to determine a heart rate using the average pixel value.

According to another aspect of the disclosure, a controller is configured to determine a respiration rate using variations in pixel values within a chest region of interest within second image data over a predefined period of time.

According to another aspect of the disclosure, a controller determines an operating boundary within first image data.

According to another aspect of the disclosure, an operating boundary outlines a periphery of a support apparatus.

According to another aspect of the disclosure, a controller is configured to monitor a position of a patient within an operating boundary by monitoring a change in position of a first selected point in first image data.

According to another aspect of the present disclosure, a patient monitoring system for a medical facility includes a first imager configured to capture first image data of a target area within a first field of view. A second imager is operably coupled to the first imager. The second imager is configured to capture second image data of the target area within a second field of view. A controller is communicatively coupled to the first imager and the second imager. The controller is configured to determine a facial region of a person in the first image data, determine a region of interest in the second image data using the facial region in the first image data, and determine vital signs information using at least one of the first image data and the second image data.

According to another aspect of the disclosure, a controller is configured to determine a calculated pixel value of a facial region.

According to another aspect of the disclosure, vital signs information includes a facial temperature. A controller is configured to determine the facial temperature using a calculated pixel value.

According to another aspect of the disclosure, a controller is configured to determine a calculated pixel value within a region of interest.

According to another aspect of the disclosure, second image data includes multiple image frames. A controller is configured to determine a calculated pixel value within a region of interest in each of the image frames.

According to another aspect of the disclosure, a controller is configured to determine data points representative of a relationship between a calculated pixel value and a number of image frames over time.

According to another aspect of the disclosure, vital signs information includes a heart rate measurement. A controller is configured to analyze data points to determine the heart rate measurement.

According to another aspect of the disclosure, a controller is configured to determine a center point in a facial region. The controller is configured to obtain a heart rate measurement each time movement of the center point exceeds a threshold.

According to another aspect of the present disclosure, a patient monitoring system includes a thermal imager configured to obtain thermal image data within a first field of view. A monochromatic imager is configured to obtain grayscale image data within a second field of view. The first field of view overlaps the second field of view. At least one imager assembly is disposed proximate to the thermal imager and the monochromatic imager. The at least one imager assembly defines a third field of view. The at least one imager assembly is coupled to an actuator configured to adjust an orientation of the at least one imager assembly.

According to another aspect of the disclosure, at least one imager assembly includes a first imager assembly disposed on a first side of a thermal imager and a second imager assembly disposed on a second side of a thermal imager.

According to another aspect of the disclosure, at least one imager assembly is configured to move via the actuator in response to sensed movement within at least one of a first field of view, a second field of view, and a third field of view.

According to another aspect of the disclosure, a first field of view and a second field of view encompass a support apparatus.

According to another aspect of the disclosure, a third field of view encompasses an area proximate to a support apparatus.

According to another aspect of the disclosure, a third field of view is configured to at least partially overlap with at least one of a first field of view and a second field of view.

According to another aspect of the present disclosure, a patient monitoring system includes a housing. A thermal imager is configured to obtain thermal image data within a first field of view. A monochromatic imager is configured to obtain monochromatic image data within a second field of view. At least one side imager assembly is selectively coupled to the housing via an actuator. The at least one side imager assembly is configured to obtain image data within a side field of view. A controller is communicatively coupled to the thermal imager, the monochromatic imager, and the at least one imager and the at least one side imager assembly. The controller is configured to activate the at least one side imager assembly in response to movement of a person within at least one of the first field of view and the second field of view toward the side field of view.

According to another aspect of the disclosure, at least one imager includes a thermal imager and a monochromatic imager.

According to another aspect of the disclosure, a controller utilizes image data captured by a thermal imager and a monochromatic imager to determine vital signs information of a person within first and second fields of view.

According to another aspect of the disclosure, a controller is configured to adjust an orientation of a side field of view relative to a housing via an actuator.

According to another aspect of the disclosure, an actuator is a ball joint actuator.

According to another aspect of the disclosure, at least one side imager assembly includes a first side imager assembly on a first side of a thermal imager and a monochromatic imager and a second side imager assembly on a second side of the thermal imager and the monochromatic imager.

According to another aspect of the disclosure, a first field of view of a thermal imager, a second field of view of a monochromatic imager, a first side field of view of the first side imager assembly, and a second side field of view of a second side imager assembly are collectively configured to extend over at least a substantial portion of a patient room.

According to another aspect of the disclosure, a controller is configured to monitor movement of a person on a support apparatus via thermal and monochromatic image data captured by a thermal imager and a monochromatic imager, respectively.

According to another aspect of the disclosure, a controller is configured to monitor movement of a person proximate a support apparatus via image data captured by first and second side imager assemblies.

According to another aspect of the disclosure, a controller is configured to determine a facial region of a person in thermal image data, determine coordinates of a head position within the facial region, and monitor movement of the person based on a change in the coordinates of the head position.

According to another aspect of the disclosure, a controller is configured to identify a caregiver within at least one of a field of view and a side field of view.

According to another aspect of the disclosure, at least one side imager assembly includes a near infrared light source.

According to another aspect of the present disclosure, a monitoring system includes a housing. A first side imager assembly is selectively coupled to a first side of the housing. The first side imager assembly defines a first side field of view to capture image data. A second side imager assembly is selectively coupled to a second side of the housing. The second side imager assembly defines a second side field of view to capture image data. At least one imager is coupled to the housing and defines a field of view to capture image data. The field of view overlaps with at least one of the first side field of view and the second side field of view. A controller is communicatively coupled with the at least one imager, the first side imager assembly, and the second side imager assembly to receive the image data. The controller is configured to monitor movement within the field of view, the first side field of view, and the second side field of view and adjust an orientation of at least one of the first side imager assembly and the second side imager assembly in response to the movement.

According to another aspect of the disclosure, the controller is configured to generate an alert in response to the movement.

According to another aspect of the disclosure, a controller adjusts an orientation of at least one of a first side imager assembly and a second side imager assembly via a ball joint actuator.

According to another aspect of the disclosure, at least one of a first side imager assembly and a second side imager assembly includes a light source.

According to another aspect of the disclosure, at least one of a first side imager assembly and a second side imager assembly is removably coupled to a housing via a connector port.

According to another aspect of the disclosure, an imager is coupled to a housing between a first side imager assembly and a second side imager assembly. The imager defines a field of view that extends between and at least partially overlaps a first side field of view and a second side field of view.

According to another aspect of the disclosure, at least one imager includes a thermal imager and a monochromatic imager. A field of view of the thermal imager and a field of view of the monochromatic imager extends between and at least partially overlaps each of a first side field of view and a second side field of view.

According to another aspect of the disclosure, a controller is configured to switch monitoring between a first side imager assembly, a second side imager assembly, and a thermal imager and a monochromatic imager in response to the movement.

According to another aspect of the disclosure, a controller is configured to determine a facial region of a person in image data of a thermal imager, determine coordinates of a head position within the facial region, monitor movement of the person based on a change in the coordinates of the head position, and determine vital signs information using the image data of the thermal imager and image data of a monochromatic imager.

According to another aspect of the present disclosure, a method of monitoring a patient includes capturing a first image with a first imager; determining a contour corresponding to a facial region of a patient within the first image; capturing a second image with a second imager; mapping a facial region of interest on the second image that corresponds with the facial region of the first image; determining a selected point within the second image; and determining whether the selected point has moved in at least one direction greater than a predefined movement threshold.

According to another aspect of the disclosure, a step of determining whether a selected point has moved includes determining whether the selected point has moved an x-direction and a y-direction.

According to another aspect of the disclosure, a method includes receiving at least one of a subsequent first image and a subsequent second image when movement of a selected point exceeds a predefined movement threshold.

According to another aspect of the disclosure, a step of determining whether a selected point has moved includes determining whether the selected point has moved in at least one direction greater than a predefined movement threshold over a predefined period of time.

According to another aspect of the disclosure, a method includes determining a first calculated pixel value within a facial region in a first image and determining a second calculated pixel value within a facial region of interest in a second image.

According to another aspect of the disclosure, a method includes determining vital signs information using at least one of a first calculated pixel value and a second calculated pixel value.

According to another aspect of the disclosure, vital signs information includes at least one of a heart rate, a facial temperature, and a respiration rate.

According to another aspect of the disclosure, a first calculated pixel value and a second calculated pixel value are each an average pixel value.

According to another aspect of the disclosure, a method includes determining a position of a person utilizing at least one of a facial region in a first image and a facial region of interest in the second image.

According to yet another aspect of the present disclosure, a monitoring system includes a controller configured to determine vital signs information from at least one of thermal image data and grayscale image data; determine movement on a support apparatus using at least one of the thermal image data and the grayscale image data; activate at least one side imager assembly based on the movement in at least one of the thermal image data and the grayscale image data; and monitor the movement in an area proximate to the support apparatus via the at least one side imager assembly.

According to another aspect of the disclosure, at least one side imager assembly includes a first side imager assembly and a second side imager assembly.

According to another aspect of the disclosure, a first side imager assembly is activated when movement is in a first direction from a support apparatus and a second side imager assembly is activated when the movement is in a second direction from the support apparatus.

According to another aspect, a contactless patient monitoring system includes a means for capturing first image data of a target area within a first field of view and a means for capturing second image data of the target area within a second field of view. A means for emitting light is operably coupled to the at least one of the means for capturing first image data and the means for capturing second image data. The means for emitting light is configured to emit light within a predetermined wavelength range. A means for processing is communicatively coupled to the means for capturing first image data, the means for capturing second image data, and the means for emitting light. The means for processing is configured to determine a facial region of a person in the first image data, determine a region of interest in the second image data that coincides with the facial region in the first image data, and determine at least one coordinate of a head position within the facial region.

It will be understood by one having ordinary skill in the art that construction of the described disclosure and other components is not limited to any specific material. Other exemplary embodiments of the disclosure disclosed herein may be formed from a wide variety of materials, unless described otherwise herein.

Related applications, for example those listed herein, are fully incorporated by reference. Descriptions within the related applications are intended to contribute to the description of the information disclosed herein as may be relied upon by a person of ordinary skill in the art. Any changes between any of the related applications and the present disclosure are not intended to limit the description of the information disclosed herein, including the claims. Accordingly, the present application includes the description of the information disclosed herein as well as the description of the information in any or all of the related applications.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A contactless patient monitoring system, comprising:
a first imager configured to capture first image data of a target area within a first field of view;
a second imager operably coupled to the first imager, wherein the second imager is configured to capture second image data of the target area within a second field of view;
an emitter operably coupled to at least one of the first imager and the second imager, wherein the emitter is configured to emit light within a predetermined wavelength range;
a housing, wherein the first imager, the second imager, and the emitter are coupled to the housing;
a side imager assembly selectively coupled to the housing via an actuator, wherein the side imager assembly is configured to obtain image data within a side field of view that extends adjacent to at least one of the first field of view and the second field of view; and
a controller communicatively coupled to the first imager, the second imager, and the emitter, wherein the controller is configured to:
determine a facial region of a person in the first image data;
determine a region of interest in the second image data that coincides with the facial region in the first image data;
determine at least one coordinate of a head position within the facial region; and
activate the side imager assembly in response to movement of the person within at least one of the first field of view and the second field of view toward the side field of view.

2. The contactless patient monitoring system of claim 1, wherein the at least one coordinate includes an x-coordinate and a y-coordinate of the head position based on an origin position within an operating boundary in the first image data.

3. The contactless patient monitoring system of claim 1, wherein the controller is configured to:
   determine whether a predefined period of time has elapsed since determining the at least one coordinate; and
   utilize at least one of the first image data and the second image data to determine vital signs information if a current elapsed time is less than the predefined period of time.

4. The contactless patient monitoring system of claim 3, wherein the controller is configured to determine a rate of change in the at least one coordinate over the predefined period of time if the predefined period of time has elapsed.

5. The contactless patient monitoring system of claim 4, wherein the controller is configured to receive a subsequent second image frame if the rate of change in the at least one coordinate exceeds a predefined threshold.

6. The contactless patient monitoring system of claim 1, wherein the controller is configured to:
   determine a central point in the region of interest in the second image data that corresponds to the at least one coordinate in the facial region;
   determine a chest region of interest in the second image data based on the central point;
   determine a calculated pixel value within the region of interest in the second image data; and
   determine at least one of a heart rate and a respiration rate using the calculated pixel value.

7. The contactless patient monitoring system of claim 6, wherein the second image data includes multiple image frames, wherein the heart rate is determined by comparing the calculated pixel value in each of the multiple image frames, and wherein the respiration rate is determined using variations in pixel values within the chest region of interest within the second image data over a predefined period of time.

8. The contactless patient monitoring system of claim 1, further comprising:
   a second side imager assembly operably coupled to the controller, wherein the side imager assembly defines the side field of view that at least partially overlaps with the first field of view of the first imager and the second side imager assembly defines a second side field of view that at least partially overlaps with the second field of view of the second imager, and wherein the controller is configured to switch monitoring between the side imager assembly, the second side imager assembly, and the first and second imagers in response to movement within the first image data, the second image data, and image data captured by the side imager assembly and the second side imager assembly.

9. A patient monitoring system, comprising:
   a housing;
   a thermal imager configured to obtain thermal image data within a first field of view;
   a monochromatic imager configured to obtain monochromatic image data within a second field of view;
   at least one side imager assembly selectively coupled to the housing via an actuator, wherein the at least one side imager assembly is configured to obtain image data within a side field of view; and
   a controller communicatively coupled to the thermal imager, the monochromatic imager, and the at least one side imager assembly, wherein the controller is configured to activate the at least one side imager assembly in response to movement of a person within at least one of the first field of view and the second field of view toward the side field of view.

10. The patient monitoring system of claim 9, wherein the controller utilizes the thermal image data captured by the thermal imager and the monochromatic image data captured by the monochromatic imager to determine vital signs information of the person within the first field of view and the second field of view.

11. The patient monitoring system of claim 9, wherein the controller is configured to adjust an orientation of the side field of view relative to the housing via the actuator.

12. The patient monitoring system of claim 9, wherein the at least one side imager assembly includes a first side imager assembly on a first side of the thermal imager and the monochromatic imager and a second side imager assembly on a second side of the thermal imager and the monochromatic imager, and wherein the first field of view of the thermal imager, the second field of view of the monochromatic imager, and a first side field of view of the first side imager assembly, and a second side field of view of a second side imager assembly are collectively configured to extend over at least a substantial portion of a patient room.

13. The patient monitoring system of claim 12, wherein the controller is configured to:
   monitor movement of the person on a support apparatus via the thermal and monochromatic image data captured by the thermal imager and monochromatic imager, respectively; and
   monitor movement of the person proximate the support apparatus via the image data captured by the first and second side imager assemblies.

14. The patient monitoring system of claim 9, wherein the controller is configured to:
   determine a facial region of the person in the thermal image data;
   determine coordinates of a head position within the facial region; and
   monitor movement of the person based on a change in the coordinates of the head position.

15. A monitoring system, comprising:
   a housing;
   a first side imager assembly selectively coupled to a first side of the housing, wherein the first side imager assembly defines a first side field of view to capture image data;
   a second side imager assembly selectively coupled to a second side of the housing, wherein the second side imager assembly defines a second side field of view to capture image data;
   at least one imager coupled to the housing and defining a field of view to capture image data, the field of view overlapping with at least one of the first side field of view and the second side field of view; and
   a controller communicatively coupled with the at least one imager, the first side imager assembly, and the second side imager assembly to receive the image data, wherein the controller is configured to:
      monitor movement within the field of view, the first side field of view and the second side field of view; and
      adjust an orientation of at least one of the first side imager assembly and the second side imager assembly in response to the movement.

16. The monitoring system of claim 15, wherein the controller adjusts the orientation of at least one of the first side imager assembly and the second side imager assembly via a ball joint actuator.

17. The monitoring system of claim 15, wherein the at least one imager includes a thermal imager and a monochromatic imager, and wherein the field of view of the thermal imager and the field of view of the monochromatic imager extends between and at least partially overlaps each of the first side field of view and the second side field of view.

18. The monitoring system of claim 17, wherein the controller is configured to switch monitoring between the first side imager assembly, the second side imager assembly, and the thermal imager and monochromatic imager in response to the movement.

19. The monitoring system of claim 18, wherein the controller is configured to:
- determine a facial region of a person in the image data of the thermal imager;
- determine coordinates of a head position within the facial region;
- monitor movement of the person based on a change in the coordinates of the head position; and
- determine vital signs information using the image data of the thermal imager and the image data of the monochromatic imager.

* * * * *